United States Patent
Servant et al.

(10) Patent No.: US 9,244,081 B2
(45) Date of Patent: Jan. 26, 2016

(54) CELL-BASED FLUORESCENT ASSAYS FOR IDENTIFYING ALPHA AND DELTA ENAC MODULATORS

(75) Inventors: Guy Servant, San Diego, CA (US); Paul Brust, San Diego, CA (US); Sumita Ray, San Diego, CA (US); Ning Hung, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 1231 days.

(21) Appl. No.: 12/301,530

(22) PCT Filed: Jul. 30, 2007

(86) PCT No.: PCT/US2007/016963
§ 371 (c)(1),
(2), (4) Date: Nov. 19, 2008

(87) PCT Pub. No.: WO2008/013969
PCT Pub. Date: Jan. 31, 2008

(65) Prior Publication Data
US 2009/0181404 A1 Jul. 16, 2009

Related U.S. Application Data

(60) Provisional application No. 60/833,783, filed on Jul. 28, 2006, provisional application No. 60/924,558, filed on May 21, 2007, provisional application No. 60/924,720, filed on May 29, 2007.

(51) Int. Cl.
*C12Q 1/02* (2006.01)
*G01N 21/77* (2006.01)
*C12N 15/70* (2006.01)
*G01N 33/68* (2006.01)
*G01N 33/50* (2006.01)
*G01N 33/566* (2006.01)

(52) U.S. Cl.
CPC ........ *G01N 33/6872* (2013.01); *G01N 33/5008* (2013.01); *G01N 33/566* (2013.01)

(58) Field of Classification Search
CPC .............. G01N 21/64; G01N 21/6402; G01N 21/6428; G01N 21/6458; G01N 21/6486; G01N 33/566; G01N 33/582; G01N 33/5008; G01N 33/5044; G01N 33/6872; G01N 2333/4706; G01N 2500/10; C07K 14/705; C12Q 2600/136
See application file for complete search history.

(56) References Cited

U.S. PATENT DOCUMENTS

2004/0110123 A1   6/2004   Maher et al.

FOREIGN PATENT DOCUMENTS

| WO | WO 02/087306 | * 11/2002 | ........... G01N 33/566 |
| WO | WO 2005015158 | * 2/2005 | |

OTHER PUBLICATIONS

Xie et al., (Am J Physiol. Renal Physiol. vol. 287:F2722-F731, 2004.).*
Birch et al., (Drugs Discovery Today. May 2004. vol. 9:410-418).*

* cited by examiner

*Primary Examiner* — Ja'Na Hines
(74) *Attorney, Agent, or Firm* — Robin L. Teskin; LeClairRyan A Professional Corporation

(57) ABSTRACT

This invention relates to improved electrophysiological assays that measure sodium conductance activity of a delta or alpha human epithelial sodium channel (ENaC) expressed in a test cell in the presence and absence of delta hENaC enhancers. The improvement comprises contacting the test cells with an amount of sodium ion, typically from at least 15 mM to 140 mM, for a time sufficient, e.g. for at least 5 minutes to an hour, prior to the test cells being screened against at least one putative enhancer. It has been surprisingly discovered that this sodium pretreatment enhances assay sensitivity, especially assays that use membrane potential or ion sensitive dyes that detect changes in conductance fluorimetrically. These enhancer compounds have potential application in modulating (enhancing) salty taste perception and for treating disorders involving aberrant hENaC function.

23 Claims, 19 Drawing Sheets

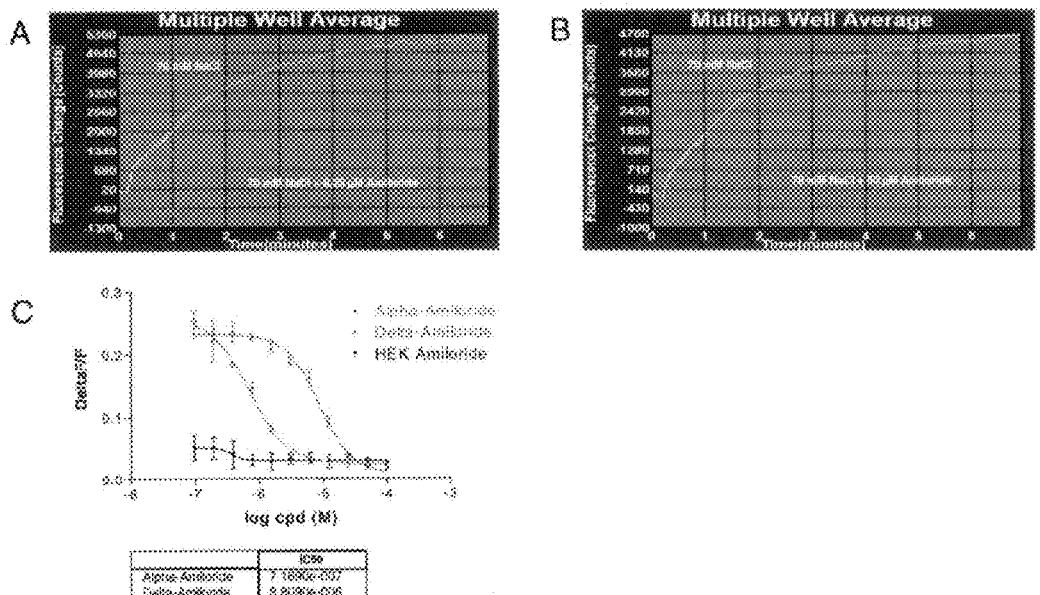

Figure 1. Panel A. Amiloride totally inhibits the NaCl-induced change in membrane potential in HEK293 cells expressing the αENaC channel. HEK 293 cells were transiently transfected with the αENaC, βENaC and γENaC subunits plasmids and were loaded with a membrane potential dye (FMP; Molecular Devices) in the absence of sodium (NaCl was replaced with NMDG) at room temperature for 1 hour. Cells were then stimulated with 70 mM NaCl with (red trace) or without (white trace) 6.25 µM amiloride. Changes in membrane potential (fluorescent signal) were monitored on a FLIPR system (Molecular Devices). Panel B. Amiloride totally inhibits the NaCl-induced change in membrane potential in HEK293 cells expressing the δENaC channel. HEK 293 cells were transiently transfected with the δENaC, βENaC and γENaC subunits plasmids and were loaded with a membrane potential dye (FMP; Molecular Devices) in the absence of sodium (NaCl was replaced with NMDG) at room temperature for 1 hour. Cells were then stimulated with 70 mM NaCl with (red trace) or without (white trace) 50 µM amiloride. Changes in membrane potential (fluorescent signal) were monitored on a FLIPR system (Molecular Devices). Panel C. Amiloride is more potent at inhibiting αENaC than δENaC. Cells were prepared and treated was described in panels A and B. Increasing concentrations of amiloride were used to assess potency at inhibiting the different forms of ENaC. The graph also shows that HEK293 cells that are not transfected with ENaC plasmids (HEK) do not show any change in membrane potential upon NaCl add back under the same experimental conditions.

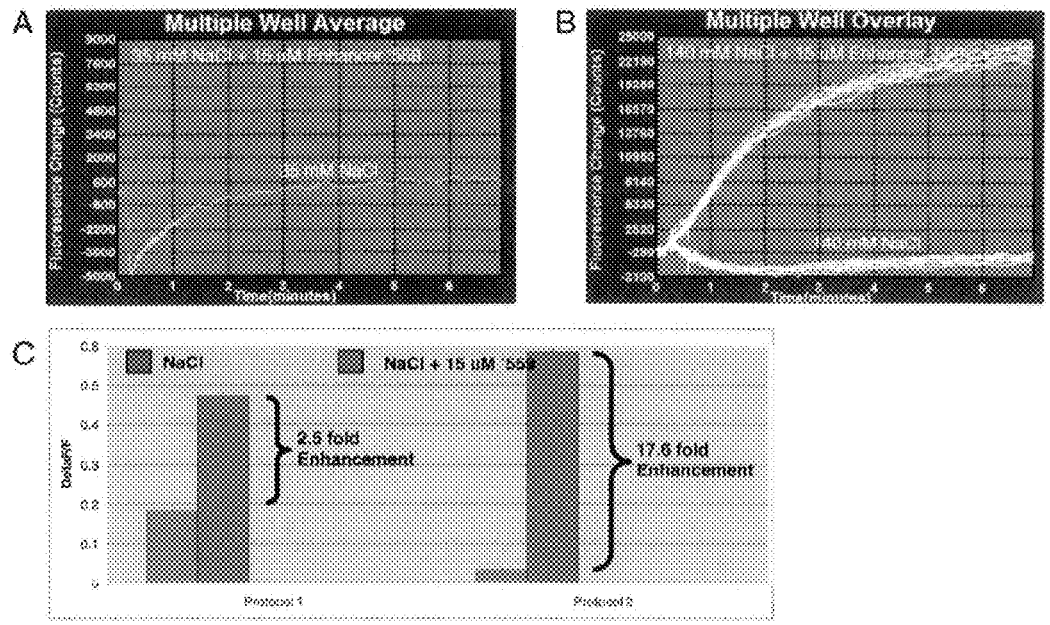

Figure 2. Panel A. The αENaC enhancer S559 increases the NaCl-induced change in membrane potential in HEK293 cells expressing the αENaC channel. HEK 293 cells were transiently transfected with the αENaC, βENaC and γENaC subunits plasmids and were loaded with a membrane potential dye (FMP; Molecular Devices) in the absence of sodium (NaCl was replaced with NMDG) at room temperature for 1 hour. Cells were then stimulated with 17.5 mM NaCl with (red trace) or without (white trace) 15 µM S559. Changes in membrane potential (fluorescent signal) were monitored on a FLIPR system (Molecular Devices). Under these conditions, S559 increased the NaCl-induced change in membrane potential by 2.5 fold indicating enhancement of αENaC (Panel C). Panel B. Dye loading in the presence of NaCl and stimulation with a greater NaCl concentration improves the S559 enhancement effect. HEK 293 cells were transiently transfected with the αENaC, βENaC and γENaC subunits plasmids and were loaded with a membrane potential dye (FMP; Molecular Devices) in the presence of 140 mM NaCl at room temperature for 1 hour. Cells were then stimulated with 140 mM NaCl with or without 15 µM S559, as indicated on the graph. Changes in membrane potential (fluorescent signal) were monitored on a FLIPR system (Molecular Devices). Under these conditions, S559 increased the NaCl-induced change in membrane potential by 17.6 fold (Panel C).

Figure 3A

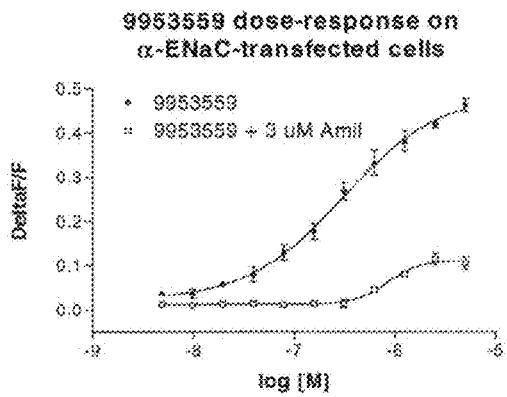

Figure 3B

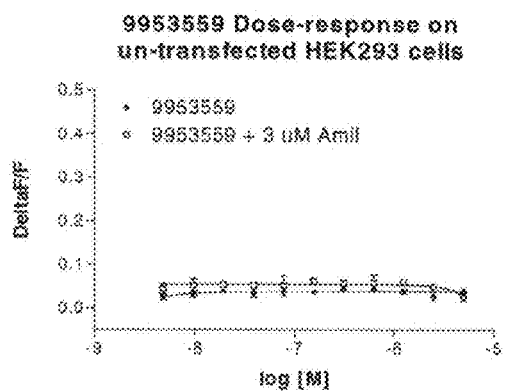

Figures 3A-B

Left Panel. Effects of the αENaC enhancer S559 are blocked by amiloride. HEK 293 cells were transiently transfected with the αENaC, βENaC and γENaC subunits plasmids and were treated as described in Figure 2; Panel B (Protocol 2). Changes in membrane potential (fluorescent signal) were monitored on a FLIPR system (Molecular Devices). Under these conditions, 3 μM amiloride almost totally abolishes S559 effects indicating that S559 enhances αENaC and not other current in HEK293 cells. Right Panel. Cells that do not express αENaC do not exhibit any effect of S559 or amiloride. HEK293 cells were transfected with a mock plasmid (pUC19) and treated as described above. Changes in membrane potential (fluorescent signal) were monitored on a FLIPR system (Molecular Devices).

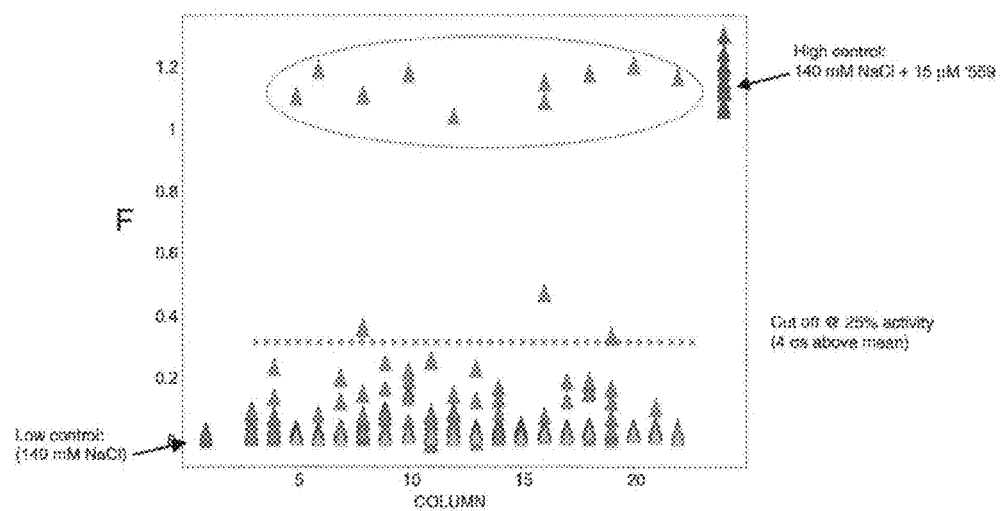

Figure 4. Robustness of the novel assay screening conditions developed for αENaC. HEK293 cells were transiently transfected with the αENaC, βENaC and γENaC subunits plasmids and were treated as described in Figure 2; Panel B (Protocol 2). A 384 well plate containing screening compounds was used to stimulate the transfected cells in the FLIPR. 10 wells of the compound plate were spiked randomly with S559 at 15 μM. The results clearly show that all the spiked wells (circled) display fluorescence counts (F) that are well above the statistical cut off (dotted line). These results indicate that these assay conditions can allow for the detection of αENaC enhancers in more than 95% of the time, in screening mode. Arrows indicate internal controls used in the screening plate.

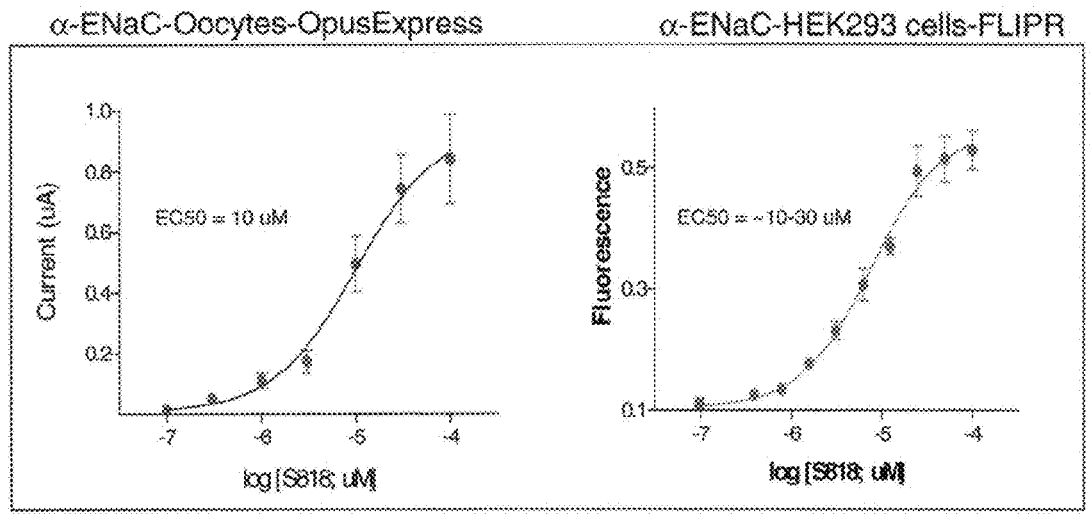

Figure 5. Improved assay conditions allow for the discovery of novel αENaC enhancers. HEK293 cells were transiently transfected with the αENaC, βENaC and γENaC subunits plasmids and were treated as described in Figure 2; Panel B (Protocol 2). 15,000 compounds at a concentration of 10 μM were tested on FLIPR using a similar plate layout as described in Figure 4. Hits above the 25% cut off activity value were then submitted for confirmation testing using current measurement in Oocytes expressing αENaC. Compound S818 showed reproducible activity in FLIPR and Oocyte assays, displaying a similar potency at enhancing αENaC.

Figure 6A

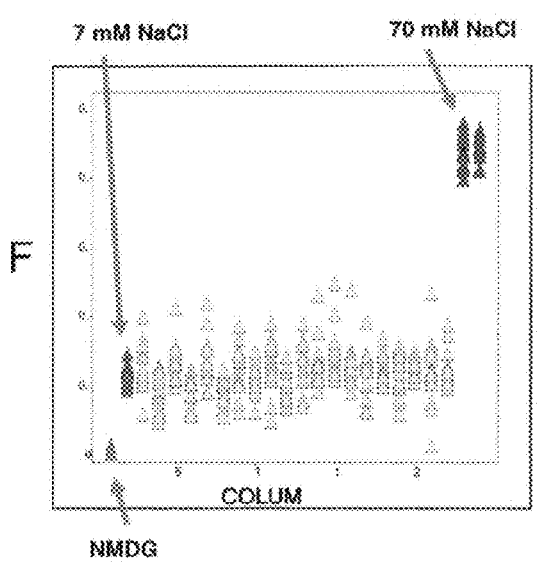

Figure 6B

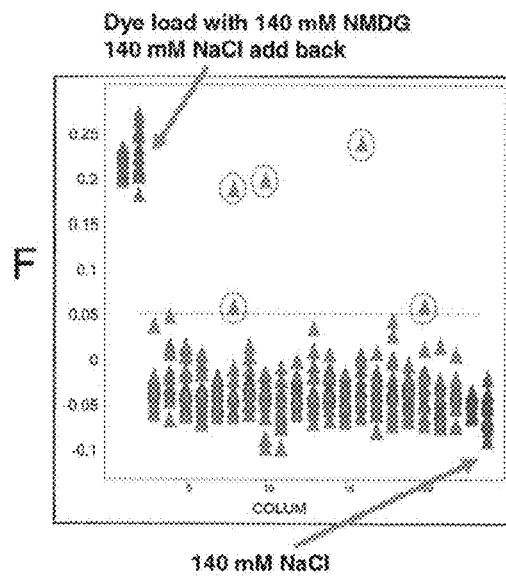

Figures 6A-B

Assay conditions developed to screen for δENaC enhancers. HEK293 cells were transiently transfected with the δENaC, βENaC and γENaC subunits plasmids and were treated as described in Figure 2; Panel B (Protocols 1 and 2). The left panel shows results of a screening plate using protocol 1. In this particular case, cells were loaded with the membrane potential dye in NMDG and compounds were added to the cells in 7 mM NaCl (instead of the 17.5 mM NaCl typically used for αENaC expressing cells). The 70 mM NaCl control represents the maximum level of δENaC stimulation measurable in this assay. The right panel shows results of a screening plate using protocol 2. In this particular case, cells were loaded with the membrane potential dye in 140 mM NaCl and compounds were added to the cells in 140 mM NaCl. In this assay, the high control value is obtained with cells loaded in NMDG and stimulated with 140 mM NaCl. This control insures that cells express a functional δENaC channel. Circled triangles correspond to primary hits.

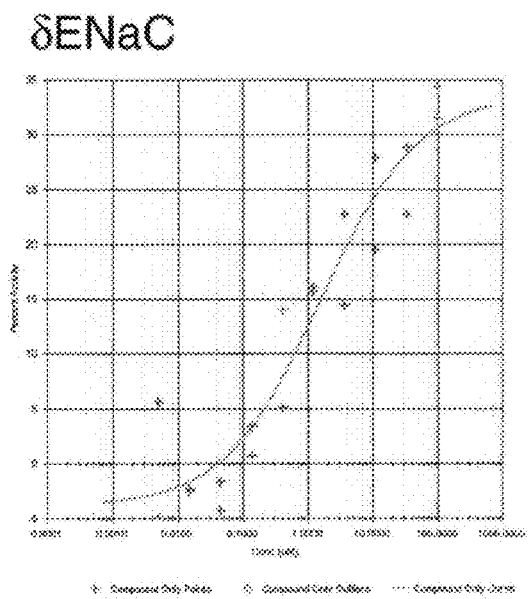
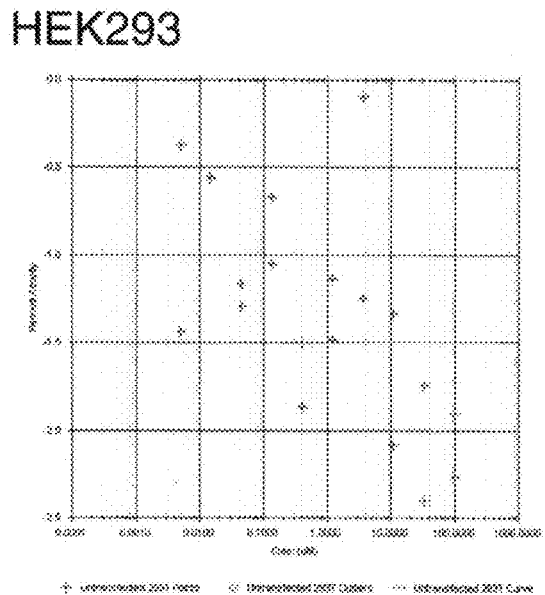

Figures 7A-B

Identification of δENaC enhancers using the novel screening assay conditions. HEK293 cells were transiently transfected with the δENaC, βENaC and γENaC subunits plasmids and were treated as described in Figure 2; Panel B (Protocol 2). The left panel shows that, in cells expressing δENaC, S16332280 induces a dose dependent change in membrane potential, indicating δENaC enhancement under these conditions. The same compound does not have any effect on un-transfected HEK293 cells (right panel).

Figure 8. Human αENaC subunit sequences

DNA sequence atggaggggaacaagctggaggagcaggactctagccctccacagtccactccagggctcatgaaggggaacaagcgtga
ggagcaggggctgggccccgaacctgcggcgccccagcagcccacggcggaggaggaggccctgatcgagttccaccgct
cctaccgagagctcttcgagttcttctgcaacaacaccaccatccacggcgccatccgcctggtgtgctcccagcacaac
cgcatgaagacggccttctgggcagtgctgtggctctgcacctttggcatgatgtactggcaattcggcctgcttttcgg
agagtacttcagctaccccgtcagcctcaacatcaacctcaactcggacaagctcgtcttcccgcagtgaccatctgca
ccctcaatccctacaggtacccggaaattaaagaggagctggaggagctggaccgcatcacagagcagacgctctttgac
ctgtacaaatacagctcttcaccactctcgtggccggctccgcagccgtcgcgacctgcgggggactctgccgcaccc
cttgcagcgcctgagggtccgcccccgcctcacggggcccgtcgagcccgtagcgtggcctccagcttgcgggacaaca
accccaggtggactggaaggactggaagatcggcttccagctgtgcaaccagaacaaatcggactgcttctaccagaca
tactcatcaggggtggatgcggtgagggagtggtaccgcttccactacatcaacatcctgtcgaggctgccagagactct
gccatccctggaggaggacacgctgggcaacttcatcttcgcctgccgcttcaaccaggtcctgcaaccaggcgaatt
actctcacttccaccacccgatgtatggaaactgctatacttcaatgacaagaacaactccaacctctggatgtcttcc
atgcctggaatcaacaacggtctgtccctgatgctgcgcgcagagcagaatgacttcattcccctgctgtccacagtgac
tggggcccgggtaatggtgcacgggcaggatgaacctgccttatggatgatggtggcttttaacttgcggcctggcgtgg
agacctccatcagcatgaggaaggaaacctggacagacttgggggcgattatggcgactgcaccaagaatggcagtgat
gttcctgttgagaaccttacccttcaaagtacacacagcaggtgtgtattcactcctgcttccaggagagcatgatcaa
ggagtgtggctgtgcctacatcttctatccgcggccccagaacgtggagtactgtgactacagaaagcacagttcctggg
ggtactgctactataagctccaggttgacttctcctcagaccacctgggctgtttcaccaagtgccggaagccatgcagc
gtgaccagctaccagctctctgctggttactcacgatggcccctcggtgacatcccaggaatgggtcttccagatgctatc
gcgacagaacaattacaccgtcaacaacaagagaaatggagtggccaaagtcaacatcttcttcaaggagctgaactaca
aaaccaattctgagtctccctctgtcacgatggtcacccttctccaaccgggcagccagtggagcctgtggttcggc
tcctcggtgttgtctgtggtggagatggctgagctcgtctttgacctgctggtcatcatgttcctcatgctgctccgaag
gttccgaagccgatactggtctccaggccgagggggcagggtgctcaggaggtagcctccacctggcatcctccctc
cttccacttctgccccacccatgtctctgtccttgtcccagccaggccctgctccctctccagccttgacagcccct
cccctgcctatgcaccctgggcccccgccatctccagggggctctgcaggggccagttcctccacctgtcctctggg
ggggccctga Protein sequence MEGNKLEEQDSSPPQSTPGLMKGNKREEQGLGPEPAAPQQPTAEEEALIEFHRSYRE
LFEFFCNNTTIHGAIRLVCSQHNRMKTAFWAVLWLCTFGMMYWQFGLLFGEYFSYP
VSLNINLNSDKLVFPAVTICTLNPYRYPEIKEELEELDRITEQTLFDLYKYSSFTTLVAGS
RSRRDLRGTLPHPLQRLVPPPHGARRARSVASSLRDNNPQVDWKDWKIGFQLCN
QNKSDCFYQTYSSGVDAVREWYRFHYINILSRLPETLPSLEEDTLGNFIFACRFNQVSC
NQANYSHFHHPMYGNCYTFNDKNNSNLWMSSMPGINNGLSLMLRAEQNDFIPLLS
TVTGARVMVHGQDEPAFMDDGFNLRPGVETSISMRKETLDRLGGDYGDCTKNGS
DVPVENLYPSKYTQQVCIHSCFQESMIKECGCAYIFYPRPQNVEYCDYRKHSSWGYC
YYKLQVDFSSDHLGCFTKCRKPCSVTSYQLSAGYSRWPSVTSQEWVFQMLSRQNNYT
VNNKRNGVAKVNIFFKELNYKTNSESPSVTMVTLLSNLGSQWSLWFGSSVLSVVEM
AELVFDLLVIMFLMLLRRFRSRYWSPCRGGRGAQEVASTLASSPPSHFCPHPMSLSLS
QPGPAPSPALTAPPPAYATLGPRPSPGGSAGASSSTCPLGGP Figure 9.  Human βENaC subunit sequences DNA sequence atgcacgtgaagaagtacctGctgaagggcctgcatcggctgcagaagggccccggctacacgtacaaggagctgctggt
gtggtactgcgacaacaccaacacccacggccccaagcgcatcatctgtgaggggcccaagaagaaagccatgtggttcc
tgctcaccctgctcttcgccgcctcgtctgctggcagtggggcatcttcatcaggacctacttgagctgggaggtcagc
gtctccctctccgtaggcttcaagaccatggacttccgcgccgtcaccatctgcaatgctagccccttcaagtattccaa
aatcaagcatttgctgaaggacctggatgagctgatggaagctgtcctggagagaatctggctcctgagctaagccatg
ccaatgccaccaggaacctgaacttctccatctggaaccacacacccctggtccttattgatgaacggaacccccaccac
cccatggtccttgatctctttggagacaaccacaatggcttaacaagcagctcagcatcagaaaagatctgtaatgccca
cgggtgcaaaatggccatgagactatgtagcctcaacaggacccagtgtaccttccggaacttcaccagtgctacccagg
cattgacagagtggtacatcctgcaggccaccaacatctttgcacaggtgccacagcaggagctagtagagatgagctac
cccggcgagcagatgatcctggcctgcctattcggagctgagccctgcaactaccggaacttcacgtccatcttctaccc
tcactatggcaactgttacatcttcaactgggggcatgacagagaaggcacttccttcggccaaccctggaactgaattcg
gcctgaagttgatcctggacataggccaggaagactacgtccccttccttgcgtccacggccggggtcaggctgatgctt
cacgagcagaggtcataccccttcatcagagatgagggcatctacGccatgtcggggacagagacgtccatcggggtact
cgtggacaagcttcagcgcatgggggagccctacagcccgtgcaccgtgaatggttctgaggtccccgtccaaaacttct
acagtgactacaacacgacctactccatccaggcctgtcttcgctcctgcttccaagaccacatgatccgtaactgcaac
tgtggccactacctgtacccactGccccgtggggagaaatactgcaacaaccgggacttcccagactgggcccattgcta
ctcagatctacagatgagcgtggcgcagagagagacctgcattggcatgtgcaaggagtcctgcaatgacacccagtaca
agatgaccatctccatggctgactggccttctgaggcctccgaggactggattttccacgtcttgtctcaggagcgggac
caaagcaccaatatcaccctgagcaggaagggaattgtcaagctcaacatctActtccaagaatttaactatcgcaccat
tgaagaatcagcagccaataacatcgtctggctgctctcgaatctgggtggccagtttggcttctggatggggggctctg
tgctgtgcctcatcgagtttggggagatcatcatcgactttgtgtggatcaccatcatcaagctggtggccttggccaag
agcctacggcagcggcgagcccaagccagCtacgctggccaccgcccaccgtggccgagctggtggaggcccacaccaa
cttcggcttccagcctgacacggccccccgcagcccaacactgggccctacccagtgagcaggccctgccatcccag
gcaccccgcccccaactatgactccctgcgtctgcagccgctggacgtcatcgagtctgacagtgagggtgatgccatc
taa Protein sequence MHVKKYLLKGLHRLQKGPGYTYKELLVWYCDNTNTHGPKRIICEGPKKKAMWFLL
TLLFAALVCWQWGIFIRTYLSWEVSVSLSVGFKTMDFPAVTICNASPFKYSKIKHLLK
DLDELMEAVLERILAPELSHANATRNLNFSIWNHTPLVLIDERNPHHPMVLDLFGD
NHNGLTSSSASEKICNAHGCKMAMRLCSLNRTQCTFRNFTSATQALTEWYILQATNI
FAQVPQQELVEMSYPGEQMILACLFGAEPCNYRNFTSIFYPHYGNCYIFNWGMTEKA
LPSANPGTEFGLKLILDIGQEDYVPFLASTAGVRLMLHEQRSYPFIRDEGIYAMSGTET
SIGVLVDKLQRMGEPYSPCTVNGSEVPVQNFYSDYNTTYSIQACLRSCFQDHMIRNC
NCGHYLYPLPRGEKYCNNRDFPDWAHCYSDLQMSVAQRETCIGMCKESCNDTQYK
MTISMADWPSEASEDWIFHVLSQERDQSTNITLSRKGIVKLNIYQEFNYRTIEESAAN
NIVWLLSNLGGQFGFWMGGSVLCLIEFGEIIIDFVWITIIKLVALAKSLRQRRAQASYA
GPPPTVAELVEAHTNFGFQPDTAPRSPNTGPYPSEQALPIPGTPFPNYDSLRLQPLDVI
ESDSEGDAI Figure 10. Human γENaC subunit sequences DNA sequence atggcacccggagagaagatcaaagccaaaatcaagaagaatctgcccgtgacgggccctcaggcgccgaccattaaaga
gctgatgcgctggtactgcctcaacaccaacacccatggctgtcgccgcatcgtggtgtcccgcggccgtctgcgccgcc
tcctctggatcgggttcacactgactgccgtggccctcatcctctggcagtgcgccctcctcgtcttctccttctatact
gtctcagtttccatcaaagtccacttccggaagctggattttcctgcagtcaccatctgcaacatcaaccctacaagta
cagcaccgttcgccaccttctagctgacttggaacaggagaccagagaggccctgaagtccctgtatggctttccagagt
cccggaagcgccgagaggcggagtcctggaactccgtctcagagggaaagcagcctagattctccaccggattccgctg
ctgatctttgatcaggatgagaaggggcaaggccagggacttcttcacagggAggaagcggaaagtcggcggtagcatcat
tcacaaggcttcaaatgtcatgcacatcgagtccaagcaagtggtgggattccaactgtgctcaaatgacacctccgact
gtgccacctacaccttcagctcgggaatcaatgccattcaggagtggtataagctacactacatgaacatcatggcacag
gtgcctctggagaagaaaatcaacatgagctattctgctgaggagctgctggtgacctgcttctttgatggagtgtcctg
tgatgccaggaatttcacgcttttCcaccacccgatgcatgggaattgctatactttcaacaacagagaaaatgagacca
ttctcagcacctccatgggggggcagcgaatatgggctgcaagtcattttgtacataaaacgaagaggaatacaacccatc
ctcgtgtcctccactggagctaaggtgatcatccatcggcaggatgagtatccttcgtcgaagatgtgggaacagagat
tgagacagcaatggtcacctctataggaatgcacctgacagagtccttcaagctgagtgagcccacagtcagtgcacgg
aggacgggagtgacgtgccaatcaggaacatctacaacgctgcctactcgctccagatctgccttcattcatgcttccag
acaaagatggtggagaaatgtgggtgtgccagtacagccagcctctacctcctgcagccaactactgcaactaccagca
gcaccccaactggatgtattgtacctaccaactgcatcgagcctttgtccaggaagagctgggctgccagtctgtgtgca
aggaagcctgcagctttaaagagtggacactaaccacaagcctggcacaatggccatctgtggtttcggagaagtggttg
ctgcctgttctcacttgggaccaaggccggcaagtaaacaaaaagctcaacaagacagacttgGccaaactcttgatatt
ctacaaagacctgaaccagagatccatcatgggagagcccagccaacagtattgagatgcttctgtccaacttcggtggcc
agctgggcctgtggatgagctgctctgttgtctgcgtcatcgagatcatcgaggtcttcttcattgacttcttctctatc
attgcccgccgccagtggcagaaagccaaggagtggtgggcctggaaacaggctcccccatgtccagaagctcccgtag
cccacagggccaggacaatccagccctggatatagacgatgacctacccacttcaactctgcttgcacctgcctccaG
ccctaggaacccaagtgcccggcacaccgccccccaaatacaataccttgcgcttggagagggccttttccaaccagctc
acagatacccagatgctAgatgagctctga Protein sequence MAPGEKIKAKIKKNLPVTGPQAPTIKELMRWYCLNTNTHGCRRIVVSRGRLRRLLWI
GFTLTAVALILWQCALLVFSFYTVSVSIKVHFRKLDFPAVTICNINPYKYSTVRHLLAD
LEQETREALKSLYGFPESRKRREAESWNSVSEGKQPRFSHRIPLLIFDQDEKGKARDFF
TGRKRKVGGSIIHKASNVMHIESKQVVGFQLCSNDTSDCATYTFSSGINAIQEWYKLH
YMNIMAQVPLEKKINMSYSAEELLVTCFFDGVSCDARNFTLFHHPMHGNCYTFNNR
ENETILSTSMGGSEYGLQVILYINEEEYNPFLVSSTGAKVIIHRQDEYPFVEDVGTEIET
AMVTSIGMHLTESFKLSEPYSQCTEDGSDVPIRNIYNAAYSLQICLHSCFQTKMVEKC
GCAQYSQPLPPAANYCNYQQHPNWMYCYYQLHRAFVQEELGCQSVCKEACSFKE
WTLTTSLAQWPSVVSEKWLLPVLTWDQGRQVNKKLNKTDLAKLLIFYKDLNQRSIM
ESPANSIEMLLSNFGGQLGLWMSCSVVCVIEIIEVFFIDFFSIIARRQWQKAKEWWAW
KQAPPCPEAPRSPQGQDNPALDIDDDLPTFNSALHLPPALGTQVPGTPPPKYNTLRL
ERAFSNQLTDTQMLDEL Figure 11.  Human δENaC subunit sequences DNA sequence atggctgagcaccgaagcatggacgggagaatggaagcagccacacggggggctctcacctccaggctgcagcccagac
gcccccaggccggggccaccatcagcaccaccaccatcaccaaggaggggcaccaggaggggctggtggagctgcccg
cctcgttccgggagctgctcaccttcttctgcaccaatgccaccatccacggcgccatccgcctggtctgctcccgcggg
aaccgcctcaagacgacgtcctgggggctgctgtccctgggagccctggtcgcgctctgctggcagctggggctcctct
tgagcgtcactggcaccgcccggtcctcatggccgtctctgtgcactcggagcgcaagctgctcccgctggtcaccctgt
gtgacgggaacccacgtcggccgagtccggtcctccgccatctggagctgctggacgagtttgccagggagaacattgac
tccctgtacaacgtcaacctcagcaaaggcagagccgccctctccgccactgtccccgccacgagccccccttccacct
ggaccgggagatccgtctgcagaggctgagccactcgggcagccgggtcagagtggggttcagactgtgcaacagcacgg
gcggcgactgctttaccgaggctacacgtcaggcgtggcggctgtccaggactggtaccacttccactatgtggatatc
ctggccctgctgcccgcgcatgggaggacagccacgggagccaggacggccacttcgtcctctctgcagttacgatgg
cctggactgccaggccgacagttccggaccttccaccaccccacctacggcagctgctacacggtcgatggcgtctgga
cagctcagcgccccggcatcacccacggagtcggctggtcctcagggttgagcagcagcctcacctccctctgctgtcc
acgctggccggcatcagggtcatggttcacggccgtaaccacacgcccttcctggggcaccacagcttcagcgtccggcc
agggacggaggccaccatcagcatccgagaggacgaggtgcaccggctcgggagcccctacggccactgcaccgccggcg
gggaaggcgtggaggtggagctgctacacaacacctcctacaccaggcaggcctgcctggtgtcctgcttccagcaActg
atggtggagacctgctcctgggctactacctccaccctctgccggcggggggctgagtactgcagctctgcccggcacc
tgcctggggacactgcttctaccgcctctaccaggacctggagacccaccggctcccctgtacctcccgctgccccaggc
cctgcagggagtctgcattcaagctctccactgggacctccaggtggccttccgccaagtcagctggatggactctggcc
acgctaggtgaacaggggctgccgcatcagagccacagacagaggagcagcctggccaaaatcaacatcgtctaccagga
gctcaactaccgctcagtggaggaggcgcccgtgtactcggtgccgcagctgtctcGgccatgggcagcctctGcagcc
tgtggtttggggcctccgtcctctccctcctggagctcctggagctgctgctcgatgcttctgcctcaccctggtgcta
ggcggccgccggctccgcagggcgtggttctcctggcccagagccagcccgcctcaggggcgtccagcatcaagccaga
ggccagtcagatgccccccgcctgcaggcggcacgtcagatgacccggagcccagcgggcctcatctccacgggtgatgc
ttccaggggttctggcggggagtTtcagccgaagagagctgggctgggccccagccccttgagactctggacacctga Protein Sequence MAEHRSMDGRMEAATRGGSHLQAAAQTPPRPGPPSAPPPPPKEGHQEGLVELPASF
RELLTFFCTNATIHGAIRLVCSRGNRLKTTSWGLLSLGALVALCWQLGLLFERHWHR
PVLMAVSVHSERKLLPLVTLCDGNPRRPSPVLRHLELLDEFARENIDSLYNVLSKGR
AALSATVPRHEPPFHLDREIRLQRLSHSGSRVRVGFRLCNSTGGDCFYRGYTSGVAAV
QDWYHFHYVDILALLPAAWEDSHGSQDGHFVLSCSYDGLDCQARQFRTFHHPTYG
SCYTVDGVWTAQRPGITHGVGLVLRVEQQPHLPLLSTLAGIRVMVHGRNHTPFLGH
HSFSVRPGTEATISIREDEVHRLGSPYGHCTAGGEGVEVELLHNTSYTRQACLVSCFQ
QLMVETCSCGYYLHPLPAGAEYCSSARHPAWGHCFYRLYQDLETHRLPCTSRCPRPC
RESAFKLSTGTSRWPSAKSAGWTLATLGEQGLPHQSHRQRSSLAKINIVYQELNYRSV
EEAPVYSVPQLLSAMGSLcSLWFGASVLSLLELLELLLDASALTLVLGGRRLRRAWFS
WPRASPASGASSIKPEASQMPPPAGGTSDDFEPSGPHLPRVMLPGVLAGVSAEESWA
GPQPLETLDT

Figure 13

Delta ENaC and PKD1L3 are expressed in different cell types. Double label in situ hybridization of primate circumvallate papilla showing that Delta ENaC (purple color; left image) does not colocalize with PKD1L3 (red; middle image). Note that purple and red colors label different cells in the merged image on the right. These data show that Delta ENaC is not expressed in sour cells. Two examples are shown (top and bottom sets of images).

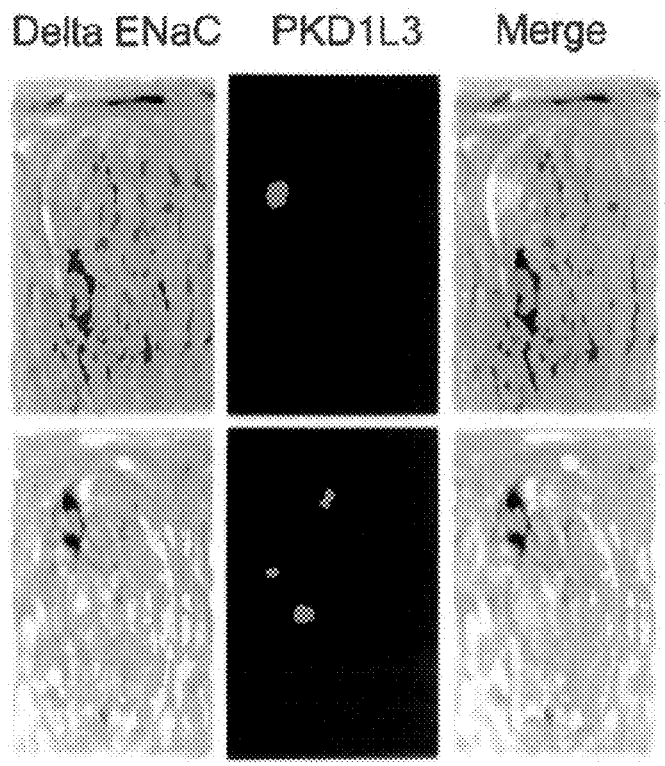

Figure 14
Delta ENaC is expressed in a subset of TRPM5 cells. Double label in situ hybridization of primate circumvallate papilla showing that Delta ENaC (purple color; left image) is expressed in a subset of TRPM5 cells (red; middle image). Note that the purple color is always associated with a red color in the merged image on the right. These data show that Delta ENaC is expressed in a subset of TRPM5 cells. Three examples are shown (top, middle and bottom sets of images).

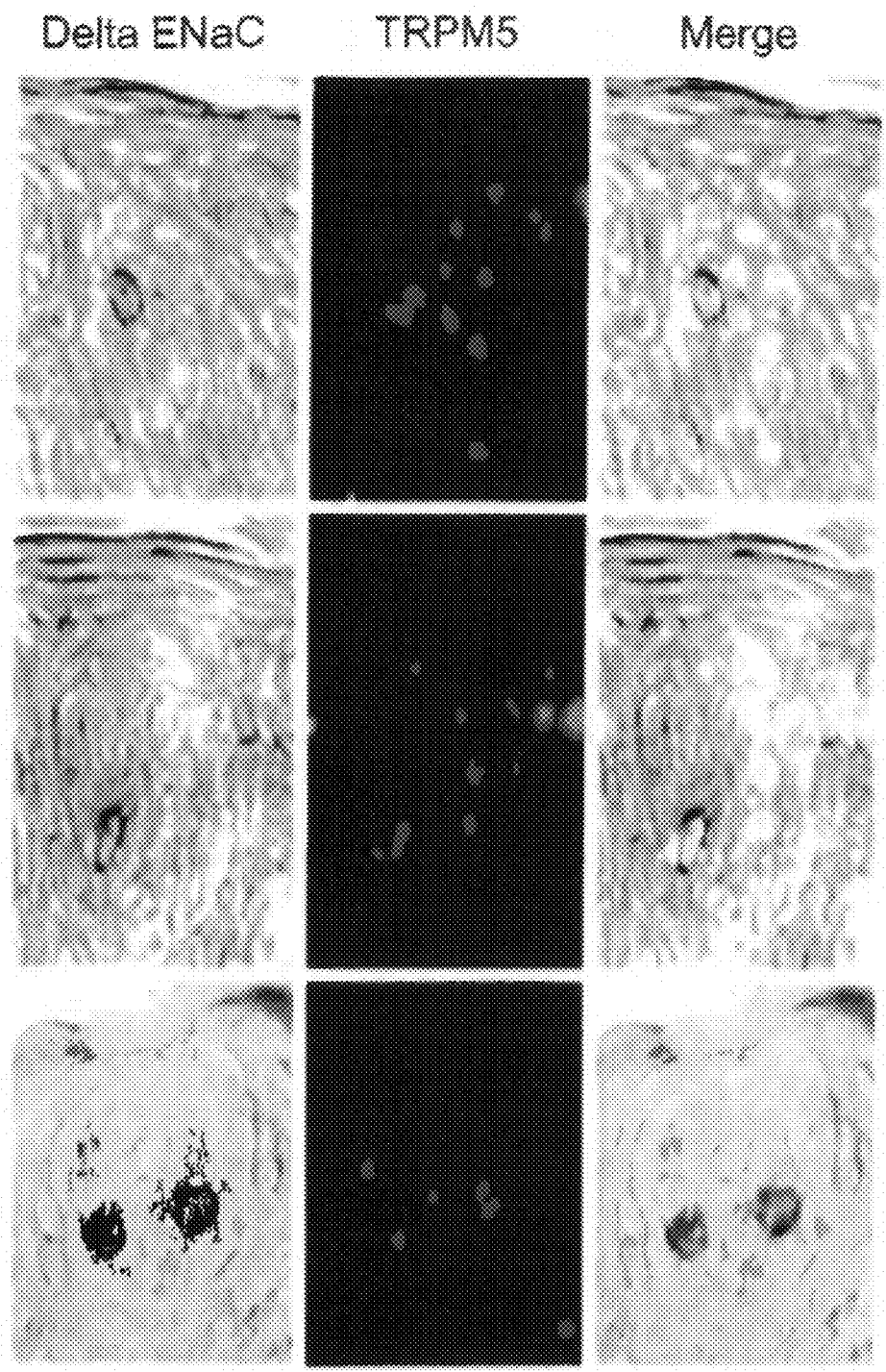

Figure 15

Alpha ENaC is expressed in PKD1L3 cells. Double label in situ hybridization of primate circumvallate papilla showing that Alpha ENaC (purple color; left image) is present in cells expressing PKD1L3 (red; middle image). Note that the red color is always associated with a purple color in the merged image on the right. These data show that Alpha ENaC is expressed in sour cells. Two taste buds are shown.

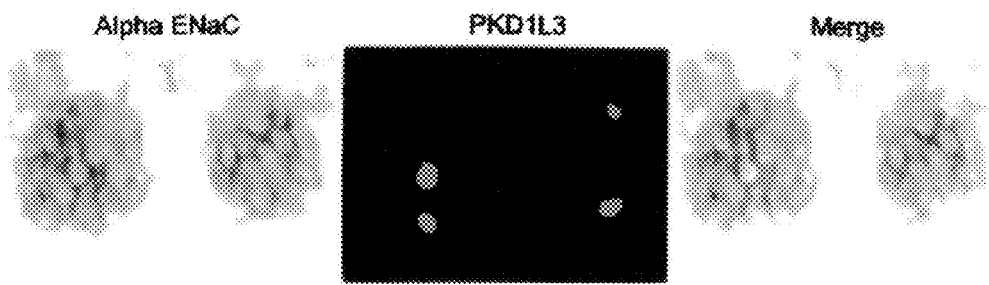

Figure 16

Alpha ENaC is expressed in TRPM5 cells. Double label in situ hybridization of primate circumvallate papilla showing that Alpha ENaC (purple color; left image) is present in cells expressing TRPM5 (red; middle image). Note that the red color is always associated with a purple color in the merged image on the right. These data show that Alpha ENaC is expressed in sweet, bitter, and umami cells. Two taste buds are shown.

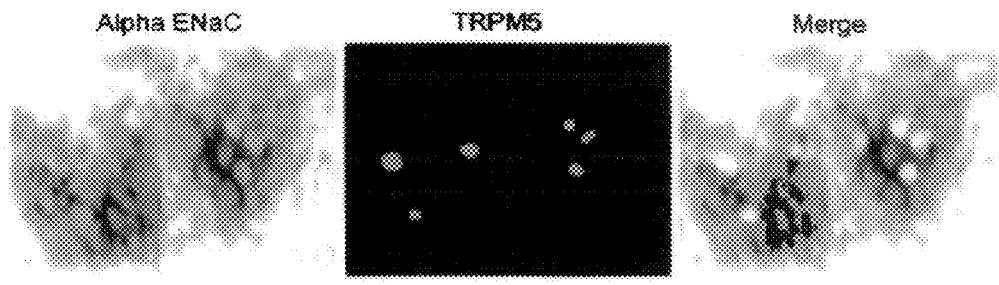

Figure 17

Delta ENaC is expressed in T1R1 umami cells. Double label in situ hybridization of primate circumvallate papilla showing that Delta ENaC (purple color; left image) colocalizes with T1R1 (red; middle image). Note that Delta ENaC cells express T1R1, a marker of umami cells (merged image on the right). However, not all T1R1 cells express Delta ENaC. Therefore, Delta ENaC labels and is expressed in a subset of umami cells. Two examples are shown (top and bottom sets of images).

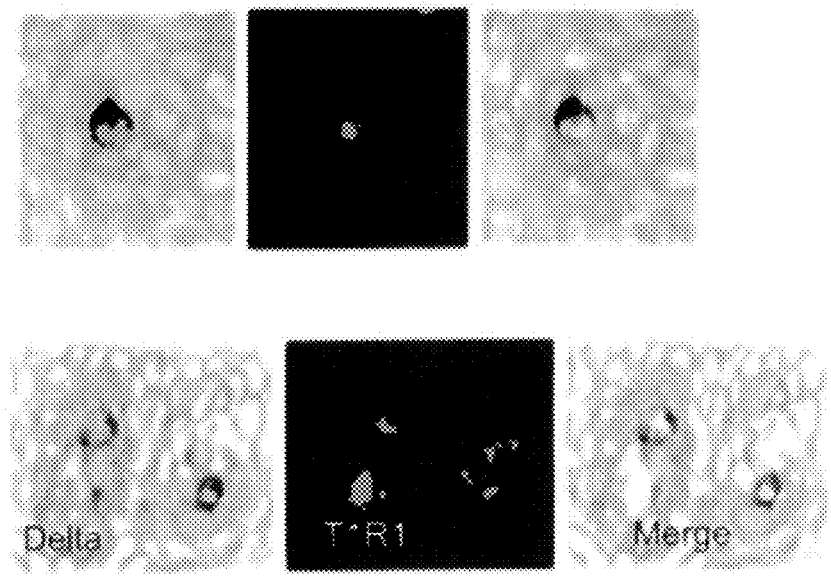

Figure 18

Delta ENaC is not expressed in T1R2 sweet cells. Double label in situ hybridization of primate circumvallate papilla showing that Delta ENaC (purple color; left image) does not colocalize with T1R2 (red; middle image). Note that purple and red colors label different cells in the merged image on the right. T1R2 is a marker of sweet cells and generally does not colocalize with Delta ENaC. Two examples are shown (top and bottom sets of images).

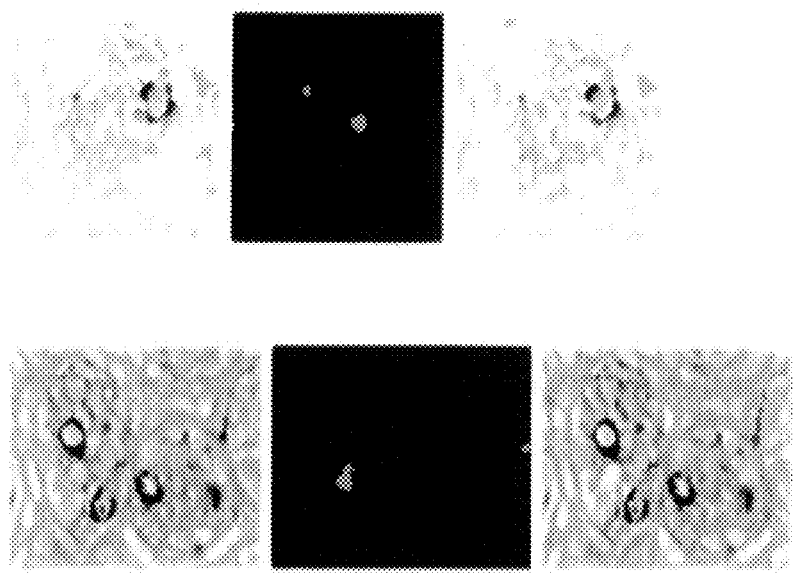

Figure 19

Delta ENaC is expressed in some T1R3 cells. Double label in situ hybridization of primate circumvallate papilla showing that Delta ENaC (purple color; left image) colocalizes with some T1R3 cells (red; middle image). Note that every Delta ENaC cell (purple) colocalizes with a T1R3 cell (red), but that every T1R3 cell does not colocalize with a Delta ENaC cell in the merged image on the right. T1R3 is a marker of sweet and umami cells. Taken together with data that Delta ENaC colocalizes with T1R1 but not significantly with T1R2, these results indicate that T1R3 cells that colocalize with Delta ENaC would be T1R1 umami cells whereas T1R3 cells that do not colocalize with Delta ENaC would largely be T1R2 sweet cells. Two examples are shown (top and bottom sets of images).

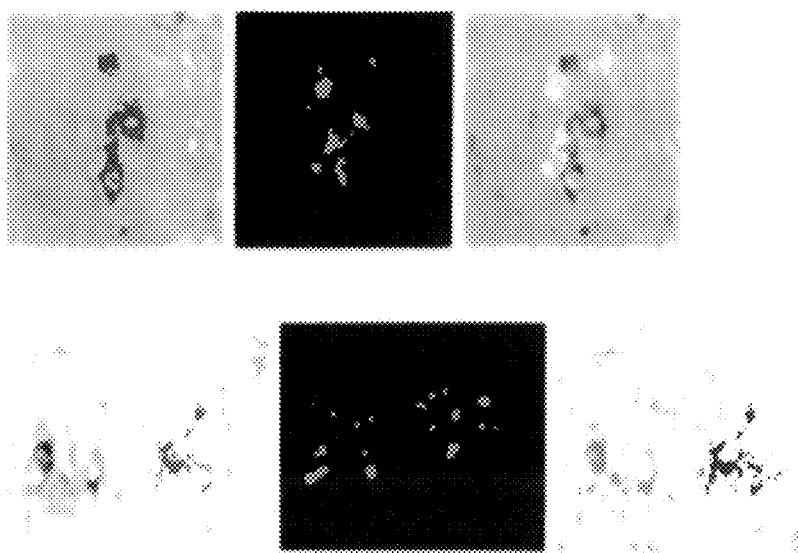

SEQUENCE LISTING

<160> NUMBER OF SEQ ID NOS: 8

<210> SEQ ID NO 1
<211> LENGTH: 2010
<212> TYPE: DNA
<213> ORGANISM: Homo sapiens

<400> SEQUENCE: 1

```
atgggaggga acaagctgga ggagcaggac tctagccctc cacagtccac tccagggctc      60
atgaagggga acaagcgtga ggagcagggg ctgggccccg aacctgcggc gccccagcag     120
cccacggcgg aggaggaggc cctgatcgag ttccaccgct cctaccgaga gctcttcgag     180
ttcttctgca acaacaccac catccacggc gccatccgcc tggtgtgctc ccagcacaac     240
cgcatgaaga cggccttctg ggcagtgctg tggctctgca cctttggcat gatgtactgg     300
caattcggcc tgcttttcgg agagtacttc agctaccccg tcagcctcaa catcaacctc     360
aactcggaca agctcgtctt ccccgcagtg accatctgca ccctcaatcc ctacaggtac     420
ccggaaatta agaggagct ggaggagctg gaccgcatca cagagcagac gctctttgac     480
ctgtacaaat acagctcctt caccactctc gtggccggct cccgcagccg tcgcgacctg     540 cggggggactc tgccgcaccc cttgcagcgc ctgagggtcc cgccccgcc tcacggggcc     600 cgtcgagccc gtagcgtggc ctccagcttg cgggacaaca accccaggt ggactggaag     660 gactggaaga tcggcttcca gctgtgcaac cagaacaaat cggactgctt ctaccagaca     720
tactcatcag gggtggatgc ggtgagggag tggtaccgct tccactacat caacatcctg     780
tcgaggctgc cagagactct gccatccctg gaggaggaca cgctgggcaa cttcatcttc     840
gcctgccgct caaccaggt ctcctgcaac caggcgaatt actctcactt ccaccacccg     900
atgtatggaa actgctatac tttcaatgac aagaacaact ccaacctctg gatgtcttcc     960
atgcctggaa tcaacaacgg tctgtccctg atgctgcgcg cagagcagaa tgacttcatt    1020
cccctgctgt ccacagtgac tgggcccgg gtaatggtgc acgggcagga tgaacctgcc    1080
tttatggatg atggtggctt taacttgcgg cctggcgtgg agacctccat cagcatgagg    1140
aaggaaaccc tggacagact tggggcgat tatgcgact gcaccaagaa tggcagtgat    1200
gttcctgttg agaacctta cccttcaaag tacacacagc aggtgtgtat tcactcctgc    1260
ttccaggaga gcatgatcaa ggagtgtggc tgtgcctaca tcttctatcc gcggccccag    1320
aacgtggagt actgtgacta cagaaagcac agttcctggg ggtactgcta ctataagctc    1380
caggttgact ctcctcaga ccacctgggc tgtttcacca gtgccggaa gccatgcagc    1440 gtgaccagct accagctctc tgctggttac tcacgatggc cctcggtgac atcccaggaa    1500
tgggtcttcc agatgctatc gcgacagaac aattacaccg tcaacaacaa gagaaatgga    1560
```

-continued

```
gtggccaaag tcaacatctt cttcaaggag ctgaactaca aaaccaattc tgagtctccc    1620
tctgtcacga tggtcaccct cctgtccaac ctgggcagcc agtggagcct gtggttcggc    1680
tcctcggtgt tgtctgtggt ggagatggct gagctcgtct ttgacctgct ggtcatcatg    1740
ttcctcatgc tgctccgaag gttccgaagc cgatactggt ctccaggccg agggggcagg    1800
ggtgctcagg aggtagcctc caccctggca tcctccccctc cttcccactt ctgccccac    1860 cccatgtctc tgtccttgtc ccagccaggc cctgctccct ctccagcctt gacagcccct    1920 cccctgcct atgccaccct gggccccgc ccatctccag ggggctctgc aggggccagt     1980
tcctccacct gtcctctggg ggggccctga                                    2010
```

<210> SEQ ID NO 2
<211> LENGTH: 669
<212> TYPE: PRT
<213> ORGANISM: Homo sapiens
<400> SEQUENCE: 2

```
Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
```

```
            290                 295                 300
Cys Tyr Thr Phe Asn Asp Lys Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
    370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
        435                 440                 445

Lys His Ser Ser Trp Gly Tyr Cys Tyr Tyr Lys Leu Gln Val Asp Phe
    450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
        515                 520                 525

Lys Glu Leu Asn Tyr Lys Thr Asn Ser Glu Ser Pro Ser Val Thr Met
    530                 535                 540

Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                565                 570                 575

Leu Val Ile Met Phe Leu Met Leu Leu Arg Arg Phe Arg Ser Arg Tyr
            580                 585                 590

Trp Ser Pro Gly Arg Gly Gly Arg Gly Ala Gln Glu Val Ala Ser Thr
        595                 600                 605

Leu Ala Ser Ser Pro Pro Ser His Phe Cys Pro His Pro Met Ser Leu
    610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
                645                 650                 655

Ala Gly Ala Ser Ser Ser Thr Cys Pro Leu Gly Gly Pro
            660                 665

<210> SEQ ID NO 3
<211> LENGTH: 1923
<212> TYPE: DNA
<213> ORGANISM: Homo sapiens

<400> SEQUENCE: 3
```

```
atgcacgtga agaagtacct gctgaagggc ctgcatcggc tgcagaaggg ccccggctac    60
acgtacaagg agctgctggt gtggtactgc gacaacacca acacccacgg ccccaagcgc   120
atcatctgtg aggggcccaa gaagaaagcc atgtggttcc tgctcaccct gctcttcgcc   180
gccctcgtct gctggcagtg gggcatcttc atcaggacct acttgagctg ggaggtcagc   240
gtctccctct ccgtaggctt caagaccatg gacttccccg ccgtcaccat ctgcaatgct   300
agccccttca gtattccaaa atcaagcat ttgctgaagg acctggatga gctgatggaa   360
gctgtcctgg agagaatcct ggctcctgag ctaagccatg ccaatgccac caggaacctg   420
aacttctcca tctggaacca cacaccctg gtccttattg atgaacggaa ccccaccac   480
cccatggtcc ttgatctctt tggagacaac cacaatggct aacaagcag ctcagcatca   540
gaaaagatct gtaatgccca cggtgcaaa atggccatga actatgtag cctcaacagg   600
acccagtgta ccttccggaa cttcaccagt gctacccagg cattgacaga gtggtacatc   660
ctgcaggcca ccaacatctt tgcacaggtg ccacagcagg agctagtaga atgagctac   720
cccggcgagc agatgatcct ggcctgccta ttcgagctg agccctgcaa ctaccggaac   780
ttcacgtcca tcttctaccc tcactatggc aactgttaca tcttcaactg gggcatgaca   840
gagaaggcac ttccttcggc caaccctgga actgaattcg gctgaagtt gatcctggac   900
ataggccagg aagactacgt ccccttcctt gcgtccacgg ccggggtcag gctgatgctt   960
cacgagcaga ggtcataccc cttcatcaga gatgagggca tctacgccat gtcggggaca  1020
gagacgtcca tcggggtact cgtggacaag cttcagcgca tgggggagcc ctacagcccg  1080
tgcaccgtga atggttctga ggtccccgtc caaaacttct acagtgacta caacacgacc  1140
tactccatcc aggcctgtct tcgctcctgc ttccaagacc acatgatccg taactgcaac  1200
tgtggccact acctgtaccc actgcccgt ggggagaaat actgcaacaa ccgggacttc  1260
ccagactggg cccattgcta ctcagatcta cagatgagcg tggcgcagag agagacctgc  1320
attggcatgt gcaaggagtc ctgcaatgac acccagtaca gatgaccat ctccatggct  1380
gactggcctt ctgaggcctc cgaggactgg attttccacg tcttgtctca ggagcgggac  1440
caaagcacca atatcaccct gagcaggaag ggaattgtca agctcaacat ctacttccaa  1500
gaatttaact atcgcaccat tgaagaatca gcagccaata acatcgtctg gctgctctcg  1560
aatctgggtg ccagtttggg cttctggatg ggggctctg tgctgtgcct catcgagttt  1620
ggggagatca tcatcgactt tgtgtggatc accatcatca agctggtggc cttggccaag  1680
agcctacggc agcggcgagc ccaagccagc tacgctggcc accgcccac cgtgccgag  1740
ctggtggagg cccacaccaa cttttggctt cagcctgaca cggcccccg cagccccaac  1800
actgggcct accccagtga gcaggccctg cccatcccag gcaccccgcc cccaactat  1860
gactccctgc gtctgcagcc gctggacgtc atcgagtctg acagtgaggg tgatgccatc  1920
taa                                                                1923

<210> SEQ ID NO 4
<211> LENGTH: 640
<212> TYPE: PRT
<213> ORGANISM: Homo sapiens

<400> SEQUENCE: 4

Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
            20                  25                  30
```

```
Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
 50                  55                  60

Trp Gln Trp Gly Ile Phe Ile Arg Thr Tyr Leu Ser Trp Glu Val Ser
 65                  70                  75                  80

Val Ser Leu Ser Val Gly Phe Lys Thr Met Asp Phe Pro Ala Val Thr
                 85                  90                  95

Ile Cys Asn Ala Ser Pro Phe Lys Tyr Ser Lys Ile Lys His Leu Leu
                100                 105                 110

Lys Asp Leu Asp Glu Leu Met Glu Ala Val Leu Glu Arg Ile Leu Ala
                115                 120                 125

Pro Glu Leu Ser His Ala Asn Ala Thr Arg Asn Leu Asn Phe Ser Ile
                130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
                180                 185                 190

Met Arg Leu Cys Ser Leu Asn Arg Thr Gln Cys Thr Phe Arg Asn Phe
                195                 200                 205

Thr Ser Ala Thr Gln Ala Leu Thr Glu Trp Tyr Ile Leu Gln Ala Thr
                210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
                245                 250                 255

Asn Tyr Arg Asn Phe Thr Ser Ile Phe Tyr Pro His Tyr Gly Asn Cys
                260                 265                 270

Tyr Ile Phe Asn Trp Gly Met Thr Glu Lys Ala Leu Pro Ser Ala Asn
                275                 280                 285

Pro Gly Thr Glu Phe Gly Leu Lys Leu Ile Leu Asp Ile Gly Gln Glu
                290                 295                 300

Asp Tyr Val Pro Phe Leu Ala Ser Thr Ala Gly Val Arg Leu Met Leu
305                 310                 315                 320

His Glu Gln Arg Ser Tyr Pro Phe Ile Arg Asp Glu Gly Ile Tyr Ala
                325                 330                 335

Met Ser Gly Thr Glu Thr Ser Ile Gly Val Leu Val Asp Lys Leu Gln
                340                 345                 350

Arg Met Gly Glu Pro Tyr Ser Pro Cys Thr Val Asn Gly Ser Glu Val
                355                 360                 365

Pro Val Gln Asn Phe Tyr Ser Asp Tyr Asn Thr Thr Tyr Ser Ile Gln
                370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
                405                 410                 415

Asn Arg Asp Phe Pro Asp Trp Ala His Cys Tyr Ser Asp Leu Gln Met
                420                 425                 430

Ser Val Ala Gln Arg Glu Thr Cys Ile Gly Met Cys Lys Glu Ser Cys
                435                 440                 445
```

```
Asn Asp Thr Gln Tyr Lys Met Thr Ile Ser Met Ala Asp Trp Pro Ser
    450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
            500                 505                 510

Asn Asn Ile Val Trp Leu Leu Ser Asn Leu Gly Gly Gln Phe Gly Phe
            515                 520                 525

Trp Met Gly Gly Ser Val Leu Cys Leu Ile Glu Phe Gly Glu Ile Ile
    530                 535                 540

Ile Asp Phe Val Trp Ile Thr Ile Lys Leu Val Ala Leu Ala Lys
545                 550                 555                 560

Ser Leu Arg Gln Arg Ala Gln Ala Ser Tyr Ala Gly Pro Pro Pro
                565                 570                 575

Thr Val Ala Glu Leu Val Glu Ala His Thr Asn Phe Gly Phe Gln Pro
            580                 585                 590

Asp Thr Ala Pro Arg Ser Pro Asn Thr Gly Pro Tyr Pro Ser Glu Gln
                595                 600                 605

Ala Leu Pro Ile Pro Gly Thr Pro Pro Asn Tyr Asp Ser Leu Arg
            610                 615                 620

Leu Gln Pro Leu Asp Val Ile Glu Ser Asp Ser Glu Gly Asp Ala Ile
625                 630                 635                 640

<210> SEQ ID NO 5
<211> LENGTH: 1950
<212> TYPE: DNA
<213> ORGANISM: Homo sapiens

<400> SEQUENCE: 5
atggcacccg agagaagat caaagccaaa atcaagaaga atctgcccgt gacgggccct      60
caggcgccga ccattaaaga gctgatgcgg tggtactgcc tcaacaccaa cacccatggc     120
tgtcgccgca tcgtggtgtc ccgcggccgt ctgcgccgcc tcctctggat cgggttcaca     180
ctgactgccg tggccctcat cctctggcag tgcgccctcc tcgtcttctc cttctatact     240
gtctcagttt ccatcaaagt ccacttccgg aagctggatt tcctgcagt caccatctgc     300
aacatcaacc cctacaagta cagcaccgtt cgccaccttc tagctgactt ggaacaggag     360
accagagagg ccctgaagtc cctgtatggc tttccagagt cccggaagcg ccgagaggcg     420
gagtcctgga actccgtctc agagggaaag cagcctagat tctcccaccg gattccgctg     480
ctgatctttg atcaggatga aagggcaag gccaggact tcttcacagg gaggaagcgg     540
aaagtcggcg gtagcatcat tcacaaggct tcaaatgtca tgcacatcga gtccaagcaa     600
gtggtgggat ccaactgtg ctcaaatgac acctccgact gtgccaccta cccttcagc     660
tcgggaatca atgccattca ggagtggtat aagctacact acatgaacat catggcacag     720
gtgcctctgg agaagaaaat caacatgagc tattctgctg aggagctgct ggtgacctgc     780
ttctttgatg gagtgtcctg tgatgccagg aatttcacgc tttccacca cccgatgcat     840
gggaattgct atactttcaa caacagagaa aatgagacca ttctcagcac ctccatgggg     900
ggcagcgaat atgggctgca agtcattttg tacataaacg aagaggaata caacccattc     960
ctcgtgtcct ccactggagc taaggtgatc atccatcggc aggatgagta tcccttcgtc    1020
gaagatgtgg aacagagat tgagacagca atggtcacct ctataggaat gcacctgaca    1080
```

-continued

```
gagtccttca agctgagtga gccctacagt cagtgcacgg aggacgggag tgacgtgcca  1140
atcaggaaca tctacaacgc tgcctactcg ctccagatct gccttcattc atgcttccag  1200
acaaagatgg tggagaaatg tgggtgtgcc cagtacagcc agcctctacc tcctgcagcc  1260
aactactgca actaccagca gcaccccaac tggatgtatt gttactacca actgcatcga  1320
gcctttgtcc aggaagagct gggctgccag tctgtgtgca aggaagcctg cagctttaaa  1380
gagtggacac taaccacaag cctggcacaa tggccatctg tggtttcgga gaagtggttg  1440
ctgcctgttc tcacttggga ccaaggccgg caagtaaaca aaaagctcaa caagacagac  1500
ttggccaaac tcttgatatt ctacaaagac ctgaaccaga gatccatcat ggagagccca  1560
gccaacagta ttgagatgct tctgtccaac ttcggtggcc agctgggcct gtggatgagc  1620
tgctctgttg tctgcgtcat cgagatcatc gaggtcttct tcattgactt cttctctatc  1680
attgcccgcc gccagtggca gaaagccaag gagtggtggg cctggaaaca ggctccccca  1740
tgtccagaag ctccccgtag cccacagggc caggacaatc cagccctgga tatagacgat  1800
gacctaccca ctttcaactc tgctttgcac ctgcctccag ccctaggaac ccaagtgccc  1860
ggcacaccgc cccccaaata caataccttg cgcttggaga gggcctttc caaccagctc  1920
acagataccc agatgctaga tgagctctga                                    1950
```

<210> SEQ ID NO 6
<211> LENGTH: 649
<212> TYPE: PRT
<213> ORGANISM: Homo sapiens

<400> SEQUENCE: 6

```
Met Ala Pro Gly Glu Lys Ile Lys Ala Lys Ile Lys Lys Asn Leu Pro
 1               5                  10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
```

```
             210                 215                 220
Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                    245                 250                 255

Leu Val Thr Cys Phe Phe Asp Gly Val Ser Cys Asp Ala Arg Asn Phe
                260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
        290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile His Arg Gln Asp Glu
                325                 330                 335

Tyr Pro Phe Val Glu Asp Val Gly Thr Glu Ile Glu Thr Ala Met Val
                340                 345                 350

Thr Ser Ile Gly Met His Leu Thr Glu Ser Phe Lys Leu Ser Glu Pro
            355                 360                 365

Tyr Ser Gln Cys Thr Glu Asp Gly Ser Asp Val Pro Ile Arg Asn Ile
        370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
                420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Ser Phe Lys Glu Trp Thr Leu
        450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
        530                 535                 540

Cys Val Ile Glu Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
                580                 585                 590

Asn Pro Ala Leu Asp Ile Asp Asp Leu Pro Thr Phe Asn Ser Ala
            595                 600                 605

Leu His Leu Pro Pro Ala Leu Gly Thr Gln Val Pro Gly Thr Pro Pro
        610                 615                 620

Pro Lys Tyr Asn Thr Leu Arg Leu Glu Arg Ala Phe Ser Asn Gln Leu
625                 630                 635                 640
```

Thr Asp Thr Gln Met Leu Asp Glu Leu
            645

<210> SEQ ID NO 7
<211> LENGTH: 1917
<212> TYPE: DNA
<213> ORGANISM: Homo sapiens

<400> SEQUENCE: 7

| | | | | | | |
|---|---|---|---|---|---|---|
| atggctgagc | accgaagcat | ggacgggaga | atggaagcag | ccacacgggg | gggctctcac | 60 |
| ctccaggctg | cagcccagac | gccccccagg | ccggggccac | catcagcacc | accaccacca | 120 |
| cccaaggagg | ggcaccagga | ggggctggtg | gagctgcccg | cctcgttccg | ggagctgctc | 180 |
| accttcttct | gcaccaatgc | caccatccac | ggcgccatcc | gcctggtctg | ctcccgcggg | 240 |
| aaccgcctca | agacgacgtc | ctgggggctg | ctgtccctgg | gagccctggt | cgcgctctgc | 300 |
| tggcagctgg | ggctcctctt | tgagcgtcac | tggcaccgcc | cggtcctcat | ggccgtctct | 360 |
| gtgcactcgg | agcgcaagct | gctcccgctg | gtcaccctgt | gtgacgggaa | cccacgtcgg | 420 |
| ccgagtccgg | tcctccgcca | tctggagctg | ctggacgagt | ttgccaggga | gaacattgac | 480 |
| tccctgtaca | acgtcaacct | cagcaaaggc | agagccgccc | tctccgccac | tgtccccgc | 540 |
| cacgagcccc | ccttccacct | ggaccgggag | atccgtctgc | agaggctgag | ccactcgggc | 600 |
| agccgggtca | gagtggggtt | cagactgtgc | aacagcacgg | gcggcgactg | cttttaccga | 660 |
| ggctacacgt | caggcgtggc | ggctgtccag | gactggtacc | acttccacta | tgtggatatc | 720 |
| ctggccctgc | tgcccgcggc | atgggaggac | agccacggga | gccaggacgg | ccacttcgtc | 780 |
| ctctcctgca | gttacgatgg | cctggactgc | caggcccgac | agttccggac | cttccaccac | 840 |
| cccacctacg | gcagctgcta | cacggtcgat | ggcgtctgga | cagctcagcg | ccccggcatc | 900 |
| acccacggag | tcggcctggt | cctcagggtt | gagcagcagc | ctcacctccc | tctgctgtcc | 960 |
| acgctggccg | gcatcagggt | catggttcac | ggccgtaacc | acgccctt | cctggggcac | 1020 |
| cacagcttca | gcgtccggcc | agggacggag | gccaccatca | gcatccgaga | ggacgaggtg | 1080 |
| caccggctcg | ggagcccccta | cggccactgc | accgccggcg | gggaaggcgt | ggaggtggag | 1140 |
| ctgctacaca | acacctccta | caccaggcag | gcctgcctgg | tgtcctgctt | ccagcaactg | 1200 |
| atggtggaga | cctgctcctg | tggctactac | ctccaccctc | tgccggcggg | ggctgagtac | 1260 |
| tgcagctctg | cccggcaccc | tgcctgggga | cactgcttct | accgcctcta | ccaggacctg | 1320 |
| gagacccacc | ggctcccctg | tacctcccgc | tgccccaggc | cctgcaggga | gtctgcattc | 1380 |
| aagctctcca | ctgggacctc | caggtggcct | tccgccaagt | cagctggatg | gactctggcc | 1440 |
| acgctaggtg | aacaggggct | gccgcatcag | agccacagac | agaggagcag | cctggccaaa | 1500 |
| atcaacatcg | tctaccagga | gctcaactac | cgctcagtgg | aggaggcgcc | cgtgtactcg | 1560 |
| gtgccgcagc | tgctctcggc | catgggcagc | tctgcagcc | tgtggtttgg | ggcctccgtc | 1620 |
| ctctccctcc | tggagctcct | ggagctgctg | ctcgatgctt | ctgccctcac | cctggtgcta | 1680 |
| ggcggccgcc | ggctccgcag | ggcgtggttc | tcctggccca | gagccagccc | tgcctcaggg | 1740 |
| gcgtccagca | tcaagccaga | ggccagtcag | atgccccgc | ctgcaggcgg | cacgtcagat | 1800 |
| gacccggagc | ccagcgggcc | tcatctccca | cgggtgatgc | ttccaggggt | tctggcggga | 1860 |
| gtttcagccg | aagagagctg | ggctgggccc | cagcccttg | agactctgga | cacctga | 1917 |

<210> SEQ ID NO 8
<211> LENGTH: 638

<212> TYPE: PRT
<213> ORGANISM: Homo sapiens

<400> SEQUENCE: 8

```
Met Ala Glu His Arg Ser Met Asp Gly Arg Met Glu Ala Ala Thr Arg
1               5                   10                  15

Gly Gly Ser His Leu Gln Ala Ala Gln Thr Pro Pro Arg Pro Gly
                20                  25                  30

Pro Pro Ser Ala Pro Pro Pro Lys Glu Gly His Gln Glu Gly
            35                  40                  45

Leu Val Glu Leu Pro Ala Ser Phe Arg Glu Leu Leu Thr Phe Phe Cys
        50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
                100                 105                 110

Arg Pro Val Leu Met Ala Val Ser Val His Ser Glu Arg Lys Leu Leu
            115                 120                 125

Pro Leu Val Thr Leu Cys Asp Gly Asn Pro Arg Arg Pro Ser Pro Val
130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
        275                 280                 285

Val Asp Gly Val Trp Thr Ala Gln Arg Pro Gly Ile Thr His Gly Val
290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
        355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400
```

-continued

```
Met Val Glu Thr Cys Ser Cys Gly Tyr Tyr Leu His Pro Leu Pro Ala
            405                 410             415
Gly Ala Glu Tyr Cys Ser Ser Ala Arg His Pro Ala Trp Gly His Cys
            420                 425             430
Phe Tyr Arg Leu Tyr Gln Asp Leu Glu Thr His Arg Leu Pro Cys Thr
        435             440                 445
Ser Arg Cys Pro Arg Pro Cys Arg Glu Ser Ala Phe Lys Leu Ser Thr
    450             455                 460
Gly Thr Ser Arg Trp Pro Ser Ala Lys Ser Ala Gly Trp Thr Leu Ala
465             470              475                         480
Thr Leu Gly Glu Gln Gly Leu Pro His Gln Ser His Arg Gln Arg Ser
            485                 490             495
Ser Leu Ala Lys Ile Asn Ile Val Tyr Gln Glu Leu Asn Tyr Arg Ser
            500                 505             510
Val Glu Glu Ala Pro Val Tyr Ser Val Pro Gln Leu Leu Ser Ala Met
            515             520                 525
Gly Ser Leu Cys Ser Leu Trp Phe Gly Ala Ser Val Leu Ser Leu Leu
        530             535             540
Glu Leu Leu Glu Leu Leu Leu Asp Ala Ser Ala Leu Thr Leu Val Leu
545             550             555                         560
Gly Gly Arg Arg Leu Arg Arg Ala Trp Phe Ser Trp Pro Arg Ala Ser
            565                 570             575
Pro Ala Ser Gly Ala Ser Ser Ile Lys Pro Glu Ala Ser Gln Met Pro
            580             585                 590
Pro Pro Ala Gly Gly Thr Ser Asp Asp Pro Glu Pro Ser Gly Pro His
        595             600                 605
Leu Pro Arg Val Met Leu Pro Gly Val Leu Ala Gly Val Ser Ala Glu
        610             615             620
Glu Ser Trp Ala Gly Pro Gln Pro Leu Glu Thr Leu Asp Thr
625             630             635
```

CELL-BASED FLUORESCENT ASSAYS FOR IDENTIFYING ALPHA AND DELTA ENAC MODULATORS

RELATED APPLICATIONS

This application relates to and claims priority to U.S. provisional application Ser. No. 60/833,783 filed on Jul. 28, 2006 and provisional application No. 60/924,558 filed on May 21, 2007 and 60/924,720 filed on May 29, 2007. These applications are incorporated by reference in their entireties herein.

SEQUENCE LISTING

The sequence listing in the filed named "67824o702401.txt" having a size of 33396 bytes that was created Nov. 19, 2008 is hereby incorporated by reference in its entirety.

FIELD OF THE INVENTION

This invention relates generally to the use of cells expressing α-ENaC or δ-ENaC in improved cell-based assays for the discovery of ENaC modulators, e.g. delta ENaC enhancers or inhibitors. More specifically the invention provides improved fluorescence assays and conditions for use therein that contact test cells that express the three alpha or the three delta ENaC subunits which are loaded with specific membrane potential or ion sensitive dyes in either the absence of sodium or in 140 mM sodium. Cell loaded in the absence of sodium show reproducible but modest effect of an ENaC enhancer when using a mixture of 17.5 mM NaCl and the enhancer as the stimulus. By contrast, cells loaded in the presence of 140 mM NaCl show a much greater magnitude of enhancement and increased assay sensitivity when using a mixture of 140 mM NaCl and the enhancer as the stimulus. Therefore, by "increased assay sensitivity" it is intended that the sodium pretreatment step results in the signal that allows for the detection of sodium conductance and the effect of the compound on ENaC activity to be greater, e.g. signal-to-background ratio is increased, relative the same assay effected without the sodium pretreatment step before contacting the test cell with the putative enhancer compound and sodium. Particularly, it has been unexpectedly discovered that these assays provide for a substantially enhanced signal-to-background ratio (5-fold higher) than assays wherein the ENaC subunit expressing test cells are loaded with dye in the absence of sodium and are then subsequently contacted with 17.5 mM sodium plus the putative enhancers. Therefore, the present invention, because of its enhanced sensitivity, should allow for the identification of alpha and delta ENaC modulators, e.g., delta ENaC enhancers or inhibitors which were undetectable using previous assays.

As described in detail infra, α-ENaC and δ-ENaC functions were monitored in HEK293 cells transiently transfected with the genes encoding the 3 α-ENaC subunits or the 3 δ-ENaC subunits and using specific membrane potential dyes (FMPs; Molecular Devices). In one protocol, cells were loaded with the specific dyes in the absence of sodium. Upon sodium add back we could detect a robust increase in the dye fluorescent signal (showing depolarization of the cells). This increase in fluorescent signal was not seen in cells transfected with a mock vector and was totally inhibited with increasing concentrations of amiloride. Under these conditions, amiloride exhibited an apparent affinity that was at least 10 fold greater on α-ENaC transfected cells relative to δ-ENaC transfected cells, as expected from published data. Using the same protocol, we found that specific α-ENaC enhancers increased the sodium-induced change in membrane potential in α-ENaC expressing cells by about 2-3 fold. Unexpectedly, it was found that the magnitude of enhancement (signal-to-background ratio) was significantly increased when a new dye-loading protocol was developed. In this protocol, cells were loaded with the membrane potential dye in the presence of 140 mM NaCl and then stimulated with the enhancers in the presence of 140 mM NaCl. These new assay conditions increased the signal-to-background ratio of the enhancers by at least 5 fold. The use of these cell based assays and improved screening conditions should allow for the discovery and development of potent α- and δENaC modulators, e.g., enhancers and inhibitors.

BRIEF DESCRIPTION OF THE INVENTION

Particularly the invention relates to improved fluorimetric assays for identifying modulators of delta ENaC which gene is a marker of specific taste cells and is involved in taste e.g., salty and/or an ancillary role in non-salty taste modalities, particularly umami taste perception.

As described infra delta ENaC is expressed in a subset of cells expressing TRPM5, a marker of sweet, bitter, and umami taste cells, but not in cells expressing PKD2L1/PKD1L3, markers of sour cells.

Also as described infra delta ENaC is specifically expressed in a subset of umami cells expressing the umami receptor T1R1 which suggests that delta ENaC can selectively regulate the biology of umami taste cells and umami taste perception and delta ENaC may also play a role in umami taste cell development and apoptosis, and umami cell signaling to nerve fibers. Therefore compounds which modulate delta ENaC may be used to regulate umami taste cell development, apoptosis and/or signaling to nerve fibers.

Also as shown infra, delta ENaC is specifically expressed in taste (umami) taste cells (which taste cells are in the digestive tract and the oral cavity, tongue, et al.) and the invention therefore embraces the use of the subject assays that screen for delta ENaC modulators to identify compounds that bind to or which modulate delta ENaC activity which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

Further as shown infra, delta ENaC is specifically expressed in certain taste cells such as umami cells, and based thereon the subject invention includes the use of the subject assays to identify compounds that may be used to treat or prevent pathological conditions involving gastrointestinal hormones involved with digestion or hunger such as gastrin, secretin, cholecystokin, gastric inhibitory peptide, glucagon-like peptide 1, amylase, or ghrelin, leptin and the like. These compounds potentially may be used to suppress or induce hunger or to modulate digestion in subjects in need thereof.

Further as shown infra, because delta ENaC is expressed in certain taste cells such as umami cells the subject fluorimetric screening assays which identify compounds that bind to or modulate the activity of delta ENaC may screen for compounds may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

Also, as shown infra, because delta ENaC is expressed in certain taste cells, e.g., umami cells the subject fluorimetric assays which screen for compounds that modulate delta ENaC or cells which express delta ENaC such as taste cells, e.g., gastrointestinal or oral cavity derived cells are useful to identify compounds that bind to or modulate delta ENaC which potentially may be used to modulate gastric reflux and diseases or conditions associated therewith such as gastroesophageal reflux disease, heartburn, Barrett's esophagus, and esophagitis.

Also as shown infra, because delta ENaC is specifically expressed in certain taste cells, e.g., umami cells the subject fluorimetric assays which screen for delta ENaC modulators e.g., using cells which express delta ENaC modulators may be used to identify compounds that bind to or which modulate delta ENaC activity and which therefore potentially may be used to treat or prevent cancers or malignancies associated with the digestive system such as by way of example cancers of the tongue, oral cavity, stomach, esophagus, small or large intestine, anus, pancreas, gall bladder, liver, or colon.

Also as shown infra, because delta ENaC is expressed specifically in certain taste cells, e.g., umami cells the subject fluorimetric assays which screen for delta ENaC modulators e.g., using cells which express delta ENaC may be used to identify compounds that bind to or which modulate the activity of delta ENaC and which compounds potentially my be use to treat or prevent appetite dysfunction and conditions associated therewith such as anorexia, bulimia, and cachexias associated therewith.

Also the subject assays may be used in assays which screen for compounds that affect sodium transport in umami taste cells and/or modulate umami receptor mediated taste.

Also because delta ENaC is specifically expressed in taste (umami) taste cells (which taste cells are in the digestive tract and the oral cavity, tongue, et al.) the invention further relates to the use of the subject fluorimetric assays to identify compounds that bind to or which modulate delta ENaC activity which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

Further because delta ENaC is expressed in taste cells such as umami cells the invention relates to the use of the subject assays to identify compounds that may be used to treat or prevent pathological conditions involving gastrointestinal hormones involved with digestion or hunger such as gastrin, secretin, cholecystokin, gastric inhibitory peptide, glucagon-like peptide 1, amylase, or ghrelin, leptin and the like. These compounds potentially may be used to suppress or induce hunger or to modulate digestion in subjects in need thereof.

Further because delta ENaC is expressed in taste cells such as umami cells the invention also relates to the use of the subject fluorimetric assays in screening to identify compounds that bind to or modulate the activity of delta ENaC which potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

Also, because delta ENaC is expressed in taste cells, e.g., umami cells the invention further relates to the use of the subject fluorimetric assays to identify compounds that bind to or modulate delta ENaC which potentially may be used to modulate gastric reflux and diseases or conditions associated therewith such as gastroesophageal reflux disease, heartburn, Barrett's esophagus, and esophagitis.

Also because delta ENaC is expressed in taste cells, e.g., umami cells the invention further relates to the use of the subject fluorimetric assays in screening assays to identify compounds that bind to or which modulate delta ENaC activity, which compounds potentially may be used to treat or prevent cancers or malignancies associated with the digestive system such as by way of example cancers of the tongue, oral cavity, stomach, esophagus, small or large intestine, anus, pancreas, gall bladder, liver, or colon.

More broadly, the invention relates to novel fluorimetric assays for identifying compounds that, can modulate the function of any cell expressing the umami receptor, including but not limited to cells in the gastrointestinal tract such as enteroendocrine cells that regulate gastric motility and peptide secretion (e.g. GLP-1: glucagon-like peptide 1; GIP: gastric inhibitory peptide).

BACKGROUND OF THE INVENTION

Epithelial sodium channels (ENaC) are members of the ENaC/degenerin family of ion channels that includes acid-sensing ion channels (ASIC) in mammals, mechanosensitive degenerin channels in worms, and FMRF-amide peptide-gated channels in mollusks (Kellenger, S. and Schild, L. (2002) Physiol. Rev. 82:735-767). ENaC mediates amiloride-sensitive apical membrane $Na^+$ transport across high resistance epithelia in numerous tissues including kidney, colon, and lung.

ENaC is known to be a heterotrimeric channel comprised of $\alpha$, $\beta$, and $\gamma$ subunits. This heterotrimeric channel has been hypothesized to be involved in human salty taste perception. Previously, assays have been developed by the present assignee using ENaC sequences to identify compounds that modulate the delta beta gamma and alpha beta gamma human ENaC to examine if these compounds will potentially modulate human salty taste perception. Also, these compounds potentially may be used to treat human pathologies involving aberrant ENaC function.

Unlike other mammals, amiloride only slightly reduces the intensity of sodium chloride taste, i.e., by about 15-20% when used at concentrations that specifically modulate ENaC function. Experiments conducted by the inventors have shown that amiloride, or the more potent amiloride derivative phenamil did not elicit a significant effect on perceived human salt intensity when tested at levels 300-fold (for amiloride) and 3000-fold (for benzamil) above IC50 values for alpha beta gamma ENaC in oocytes (equivalent to 10-fold for amiloride and 100-fold for benzamil over IC50 values for delta beta gamma ENaC in oocytes). Thus, additional non-ENaC genes are likely involved in human taste and other biological functions.

This invention relates to fluorescent assays that identify compounds that modulate (enhance) ENaC in test cells which express a functional delta or alpha sodium epithelial channel, preferably the human alpha or delta ENaC, and the use thereof e.g., to modulate human umami or salty taste perception or other biological functions involving delta ENaC or alpha ENaC such as described herein. More specifically the invention provides improved fluorimetric assays and conditions for use therein that contact test cells which preferably express the three alpha or delta ENaC subunits with specific membrane potential or ion sensitive dyes under conditions that result in a profound enhancement in fluorescence signal relative to prior assays. As shown infra, it has been surprisingly discovered that when ENaC expressing cells are loaded with membrane potential dye in the presence of a sufficient amount of sodium and for a sufficient time and the test cells thereafter contacted with at least one putative ENaC enhancer that a substantially enhanced fluorimetric signal is generated than prior assays wherein sodium was absent or was at most 17.5 mM during membrane potential dye loading and prior to contacting the test cells with the putative enhancer. Thus this invention should provide for the identification of ENaC enhancers undetectable in prior assays.

Based thereon, improved assays have been developed which are disclosed herein to identify compounds that modulate the alpha and delta human ENaC. These compounds will be useful in modulating human taste, e.g., umami or human salty taste perception. Also, as described above these compounds may be used to treat human pathologies involving ENaC function.

Particularly Also the invention relates to the use of the subject novel assays for identifying compounds that enhance or inhibit delta ENaC can selectively modulate umami taste function and response to umami tastants.

Further the invention relates to use of the subject improved assays for identifying compounds that enhance or inhibit delta ENaC which can modulate umami taste cell development and apoptosis.

Further, the invention relates to the use of the subject improved assays to identify compounds that enhance or inhibit delta ENaC can modulate the function of any cell expressing the umami taste receptor including by way of example cells in the gastrointestinal tract such as enteroendocrine cells that regulate gastric motility and peptide secretion or digestion (e.g., GLP-1, glucagon-like peptide 1, GIP (gastric inhibitory peptide), secretin, amylase, cholecystokinin and the like).

Further, the invention relates to the use of the subject assays to identify compounds that enhance or inhibit alpha ENaC which can modulate sweet, bitter, umami and sour taste function and responses to sweet, bitter, umami, and sour tastants. This is predicated in part on the observation that salt (sodium) makes food taste better which may relate to sodium ions flowing through alpha ENaC ion channels and depolarizing sweet, bitter, umami, and sour taste cells, thereby leading to their activation and transmission of signals to the brain indicating enhanced sweet, bitter, umami, and sour taste perception.

Also the invention relates to the use of the subject assays to identify compounds that bind to or which modulate delta ENaC activity which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

Also the invention relates to the discovery that because delta ENaC is expressed in taste cells such as umami cells the invention relates to the use of the subject assays to identify compounds that may be used to treat or prevent pathological conditions involving gastrointestinal hormones involved with digestion or hunger such as gastrin, secretin, cholecystokin, gastric inhibitory peptide, glucagon-like peptide 1, amylase, or ghrelin, leptin and the like. These compounds potentially may be used to suppress or induce hunger or to modulate digestion in subjects in need thereof.

Also because delta ENaC is expressed in taste cells such as umami cells the invention also relates to the use of the subject assays to identify compounds that bind to or modulate the activity of delta ENaC which compounds potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

Also, because delta ENaC is expressed in taste cells, e.g., umami cells the invention further relates to the use of the subject assays which use delta ENaC or cells which express delta ENaC such as taste cells, e.g., gastrointestinal or oral cavity derived cells in screening assays to identify compounds that bind to or modulate delta ENaC which potentially may be used to modulate gastric reflux and diseases or conditions associated therewith such as gastroesophageal reflux disease, heartburn, Barrett's esophagus, and esophagitis.

Also because delta ENaC is expressed in taste cells, e.g., umami cells the invention further relates to the use of the subject assays which use delta ENaC or cells which express delta ENaC in screening assays to identify compounds that bind to or which modulate delta ENaC activity and which therefore potentially may be used to treat or prevent cancers or malignancies associated with the digestive system such as by way of example cancers of the tongue, oral cavity, stomach, esophagus, small or large intestine, anus, pancreas, gall bladder, liver, or colon.

Also because delta ENaC is expressed in taste cells, e.g., umami cells the invention further relates to the use of the subject assays that use delta ENaC or cells which express delta ENaC in screening assays to identify compounds that bind to or which modulate the activity of delta ENaC which compounds potentially my be use to treat or prevent appetite dysfunction and conditions associated therewith such as anorexia, bulimia, and cachexias associated therewith.

BACKGROUND OF THE INVENTION

Epithelial sodium channels (ENaC) are members of the ENaC/degenerin family of ion channels that includes acid-sensing ion channels (ASIC) in mammals, mechanosensitive degenerin channels in worms, and FMRF-amide peptide-gated channels in mollusks (Kellenger, S, and Schild, L. (2002) Physiol. Rev. 82:735-767). ENaC mediates apical membrane $Na^+$ transport across high resistance epithelia in numerous tissues including kidney, colon, and lung.

ENaC is an epithelial sodium channel that is essential for normal sodium homeostasis and sodium balance in mammals. ENaC is also thought to play a role in the detection of saltiness in rodents. ENaC is thought to form two different channels presenting different sensitivities to some pharmacological agents. ENaC is known to be a heterotrimeric channel comprised of $\alpha$, $\beta$, and $\gamma$ subunits. T The alpha ENAC channel is composed of three subunits including alpha, beta and gamma ENaC whereas the delta ENaC is composed of three subunits including delta, beta and gamma ENaC subunits. The alpha ENaC is known to show a high sensitivity to the ENaC blocker amiloride.

Each of the ENaC subunits are expressed in human and rodent taste cells. Consequently, this heterotrimeric channel has also been hypothesized to be involved in human salty taste perception. Additionally, as discussed above this channel is involved in the maintenance of extracellular volume and blood pressure, absorption of fluid from the lungs during late stages of gestation, and transduction of salt taste. (See e.g., Rossier, B. C. et al., Annu. Rev. Physiol. 62:877-897 (2002); Alvaraz et al. Annu. Rev. Physiol. 62:573-594 (2000); and Bigiani et al., Prog. Biophys. Mol. Biol. 83:193-225 (2003)).

It is also known that mutations in the human ENaC (hENaC), particularly gain of function mutations result in hypertension due to increased renal $Na^+$ reabsorption in Liddle's syndrome (Schild et al., Proc. Natl. Acad. Sci., USA 92:5699-5703 (1995); Shirnkets et al., Cell 79:407-414 (1994); and Snyder et al., Cell 83:969-98 (1995)). By contrast, it is known that hENaC loss of function mutations result in salt-wasting due to decreased renal $Na^+$ reabsorption in pseudohypoaldosteronism type I (PHA1). (See Grunder et al., EMBO. J. 16:899-907 (1997); and Chang et al., Nat. Genet. 12:248-253 (1996)).

OBJECTS OF THE INVENTION

It is an object of this invention disclosure to provide improved screening assays that identify human delta or alpha human epithelial sodium channel (ENaC) modulators e.g., enhancers and inhibitors.

It is a specific object of the invention to provide improved cell-based fluorescent assays with fluorescence readout that measure sodium conductance of delta beta gamma or alpha beta gamma human ENaC channels.

It is a specific object of the invention to provide ENaC screening assays which provide for higher sensitivity to previous assays and which identify ENaC enhancers undetectable by prior assays.

It is another object of the invention to identify delta ENaC specific enhancers using these improved assays that modulate, preferably enhance human salty taste perception.

It is another object of the invention to use the subject assays to identify compounds that enhance or inhibit delta ENaC can selectively modulate umami taste function and response to umami tastants.

It is another object of the invention to use the subject assays to identify compounds that enhance or inhibit delta ENaC which may be used to modulate umami taste cell development and apoptosis.

It is another object of the invention to use the subject assays to identify compounds that enhance or inhibit delta ENaC which can modulate the function of any cell expressing the umami taste receptor including by way of example cells in the gastrointestinal tract such as enteroendocrine cells that regulate gastric motility and peptide secretion or digestion (e.g., GLP-1, glucagon-like peptide 1, GIP (gastric inhibitory peptide), secretin, amylase, cholecystokinin and the like).

Further, it is another object of the invention because to alpha ENaC is expressed in sweet, bitter, umami, and sour taste cells to use the subject assays to identify compounds that enhance or inhibit alpha ENaC can modulate sweet, bitter, umami and sour taste function and responses to sweet, bitter, umami, and sour tastants. In this manner, the observation that salt (sodium) makes food taste better may relate to sodium ions flowing through alpha ENaC ion channels and depolarizing sweet, bitter, umami, and sour taste cells, thereby leading to their activation and transmission of signals to the brain indicating enhanced sweet, bitter, umami, and sour taste perception.

Also it is an object of the invention, because delta ENaC is specifically expressed in taste (umami) taste cells (which taste cells are in the digestive tract and the oral cavity, tongue, et al.) to use the subject assays to screen for compounds that bind to or which modulate delta ENaC activity which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

Also it is another object of the invention to use the inventive assays to identify compounds that may be used to treat or prevent pathological conditions involving gastrointestinal hormones involved with digestion or hunger such as gastrin, secretin, cholecystokin, gastric inhibitory peptide, glucagon-like peptide 1, amylase, or ghrelin, leptin and the like. These compounds potentially may be used to suppress or induce hunger or to modulate digestion in subjects in need thereof.

Also it is another object of the invention to use the subject assays in screening for compounds that bind to or modulate the activity of delta ENaC which potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

Also, it is an object of the invention relates to use the subject assays in screening for compounds that bind to or modulate delta ENaC which potentially may be used to modulate gastric reflux and diseases or conditions associated therewith such as gastroesophageal reflux disease, heartburn, Barrett's esophagus, and esophagitis.

Also it is an object of the invention to use the subject screening assays to identify compounds that bind to or which modulate delta ENaC activity and which therefore potentially may be used to treat or prevent cancers or malignancies associated with the digestive system such as by way of example cancers of the tongue, oral cavity, stomach, esophagus, small or large intestine, anus, pancreas, gall bladder, liver, or colon.

Also it is an object of the invention to use the subject screening assays to identify compounds that bind to or which modulate the activity of delta ENaC which compounds potentially my be use to treat or prevent appetite dysfunction and conditions associated therewith such as anorexia, bulimia, and cachexias associated therewith.

As described in greater detail infra, experiments performed by the inventors were effected wherein alpha ENaC and delta ENaC functions were measured in test HEK293 cells transiently transfected with genes encoding the three alpha ENaC subunits or the three delta ENaC subunits and specific membrane potential dyes. (FMP; Molecular Devices). In one protocol, cells were loaded with the specific dyes in the absence of sodium. Upon sodium add back a robust increase in the dye fluorescent signal was detected (showing depolarization of the cells). This increase in fluorescent signal was not seen in cells transfected with a mock vector and was totally inhibited with increasing concentrations of amiloride. Under these conditions amiloride exhibited an apparent affinity that was at least 10-fold greater on alpha ENaC transfected cells relative to delta ENaC transfected cells, as anticipated from published data. Also, using the same protocol, it was found that specific alpha ENaC enhancers increased the sodium-induced change in membrane potential in alpha-ENaC expressing cells by at least about 2-3-fold. Unexpectedly, it was found that the magnitude of enhancement was significantly increased by modification of the dye-loading protocol. Particularly, it was found that when cells were loaded with the membrane potential dye in the presence of sufficient amount of sodium, e.g., about 140 mM NaCl and then stimulated with the enhancer or enhancers in the presence of sodium (e.g., about 140 mM NaCl) that these loading conditions resulted in about a 5-fold enhancement in the fluorescent signal relative to assays wherein membrane potential dye loading was effected in the absence of sodium. Consequently, these improved assays are much more sensitive and should identify ENaC modulators (enhancers and inhibitors) undetectable by previous assays. Thus, the invention provides improved assays for identifying modulators of the human delta beta gamma and human alpha beta gamma ENaC heterotrimeric channel. The compounds identified and their derivatives potentially can be used as modulators of taste, e.g. human umami or salty taste in foods, beverages and medicinals for human or animal consumption. Also, such compounds and their derivatives potentially may be used to treat diseases involving aberrant ENaC function.

BRIEF DESCRIPTION OF THE FIGURES

FIG. 1A-C contains the results of three fluorescent assays. FIG. 1A shows that amiloride totally inhibits the NaCl-induced change in potential in HEK293 cells expressing a functional heterotrimeric alphaENaC channel. FIG. 1B shows that amiloride totally inhibits the NaCl-induced change in membrane potential in cells expressing the heterotrimeric deltaENaC channel. FIG. 1C shows hat amiloride is more potent at inhibiting alphaENaC than deltaENaC.

FIG. 2A-2C contains the results of fluorescent experiments using a proprietary ENaC enhancer. FIG. 2A shows that this enhancer S559 increases the NaCl induced change in membrane potential in HEK293 cells expressing a functional heterotrimeric alphaENaC channel. FIG. 2B shows that dye loading in the presence of NaCl and stimulation with a greater NaCl concentration improves the S559 enhancement effect. FIG. 2C contains a graph which shows that under these loading conditions that S559 increased the NaCl-induced change in membrane potential by from 2.5 fold to 17.6 fold.

FIGS. 3A and 3B contain dose-response experiments in alpha-ENaC transfected cells and untransfected cells. FIG. 3A shows that the effects of the S559 enhancer are blocked by amiloride. FIG. 3B shows that cells that do not express alphaENaC do not exhibit any effect of S559 or amiloride.

FIG. 4 contains the results of fluorescent assays that reveal the robustness of the novel and improved assays provided herein that loading ENaC transfected cells with dye in the presence of a sufficient amount of sodium allows for the repetitive identification of an enhancer in screening mode.

FIG. 5 contains the results of fluorescent assays effected in ENaC transfected oocytes and HEK293 cells that confirm that the improved assays of the invention allow for the discovery of novel ENaC enhancers.

FIGS. 6A and 6B shows the assay conditions developed to screen for human deltaENaC channel enhancers. In FIG. 6A deltaENaC transfected HEK293 test cells were loaded with a membrane potential dye (FMP; Molecular Devices) in NMDG and then stimulated with 7 mM NaCl and the compound. In FIG. 6B the same transfected HEK293 test cells were loaded with the membrane potential dye in the presence of 140 mM NaCl and then stimulated with the same enhancer compounds in 140 mM NaCl.

FIGS. 7A and 7B shows the results of additional fluorescent assays effected using deltaENaC transfected HEK293 cells according to the invention and a control (untransfected HEK293 cells). In these experiments a deltaENaC enhancer compound was successfully identified as shown in FIG. 7A using assays including the subject increased sodium loading conditions. By contrast in FIG. 7B (negative control) the same enhancer compound did not have any effect on the untransfected HEK293 cells.

FIG. 8 contains the human alpha ENaC DNA (SEQ ID NO:1) and protein (SEQ ID NO:2) subunit sequences.

FIG. 9 contains the human beta ENaC DNA (SEQ ID NO:3) and protein (SEQ ID NO:4) subunit sequences.

FIG. 10 contains the human gamma ENaC DNA (SEQ ID NO:5) and protein (SEQ ID NO:6) subunit sequences.

FIG. 11 contains the human delta ENaC DNA (SEQ ID NO:7) and protein (SEQ ID NO:8) subunit sequences.

FIG. 13 contains in situ hybridization experiments with primate circumvallate cells showing that delta ENaC is not expressed in taste cells that express PKD1L3 (sour taste cells).

FIG. 14 contains in situ hybridization experiments with primate circumvallate papilla cells showing that delta ENaC is expressed in a subtype of TRPM5 cells that are known to be involved in sweet, bitter, and umami taste.

FIG. 15 contains in situ hybridization experiments with primate circumvallate papilla cells showing that alpha ENaC is expressed in PKD1L3 cells that are known to be involved in sour taste.

FIG. 16 contains in situ hybridization experiments with primate circumvallate papilla cells showing that alpha ENaC is expressed in TRPM5 cells that are known to be involved in sweet, bitter, and umami taste FIG. 17 contains in situ hybridization experiments with primate circumvallate cells showing that delta ENaC is expressed in T1R1 umami taste cells.

FIG. 18 contains in situ hybridization experiments in primate circumvallate cells showing that delta ENaC is not expressed in T1R2 sweet cells.

FIG. 19 contains in situ hybridization experiments in primate circumvallate cells showing that delta ENaC is expressed in some T1R3 cells.

SUMMARY OF INVENTION

Figure 12:
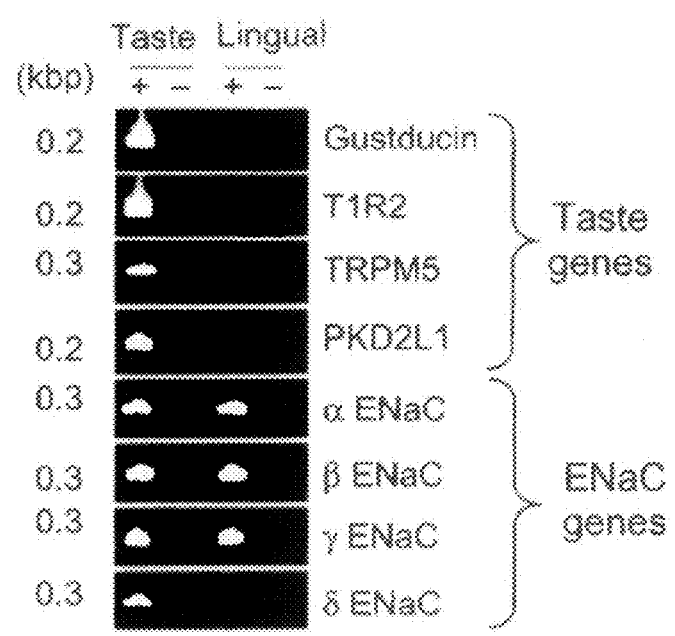
FIG. 12: This figure contains PCR experiments with primate circumvallate papilla cells showing that delta ENaC, but not alpha, beta, or gamma ENaC is specifically expressed in taste cells but not lingual cells.

The subject invention relates to improved screening assays for identifying human delta and alpha epithelial sodium channel (ENaC) modulators, e.g., enhancers.

Based on the foregoing, the present invention uses cell-based assays to identify delta and alpha human ENaC modulators (enhancers). These compounds have potential application at least in modulating human umami or salty taste perception. Compounds identified in the subject electrophysiological assays and their biologically acceptable derivatives are to be tested in human taste tests using human volunteers to confirm their effect on human umami or salty taste perception or on other ENaC related functions. Alternatively, these compounds and their derivatives potentially may be used to treat conditions or to modulate other physiological functions such as gastrointestinal and metabolic functions involving ENaC activity such as the specific ENaC related conditions or diseases identified herein.

As discussed further infra, these cell-based assays preferably use high throughput screening platforms to identify compounds that modulate (enhance) ENaC activity using cells that express human delta beta gamma or alpha beta gamma ENaC ENaCs. The sequences of these respective human delta, beta and gamma subunits are provided in FIGS. 8-11 and contained in SEQ ID NO: 1-8. Additionally, these sequences may be modified for example to introduce silent mutations or mutations having a functional effect such as defined mutations that affect sodium ion influx. The inventive assays will preferably comprise electrophysiologic assays effected in amphibian oocytes or assays using mammalian cells that express a human delta beta gamma or alpha beta gamma ENaC using fluorescent ion sensitive dyes or membrane potential dyes, e.g., sodium-sensitive dyes wherein sodium is present during dye loading and/or is present prior to contacting with known or putative ENaC enhancer compounds. For example, compounds that modulate ENaC are identified by screening using electrophysiological assays effected with oocytes that express a human delta beta gamma ENaC (e.g., patch clamping or two electrode voltage clamping).

Alternatively, as shown in the experiments infra fluorescent assays are effected using HEK293 cells transfected transiently or stably with nucleic acid sequences encoding the human alpha beta gamma ENaC subunits or the delta beta gamma ENaC subunits wherein these cells are loaded with membrane or ion potential dye and sodium (NaCl) at concentrations sufficient to enhance readout (fluorescence), (e.g. on the order of 140 mM NaCl) relative to when loading is effected in the absence of sodium). Still alternatively, compounds that modulate ENaC may be detected by ion flux assays, e.g., radiolabeled-ion flux assays or atomic absorption spectroscopic coupled ion flux assays. As disclosed supra, these ENaC enhancers have potential application in modulating human salty taste perception or for modulating other biological processes involving aberrant or normal ENaC function.

The subject cell-based assays use cells which are transfected or transformed with the wild-type ENaC nucleic acid subunit sequences contained in FIGS. 8-11, or mutated forms or allelic variants thereof which are expressed in desired cells, preferably human cells such as HEK293 cells, oocytes, or other human or mammalian cells conventionally used in screens for identifying ion channel modulatory compounds under conditions which result in functional ENaC channel, i.e. an ion channel which is responsive to sodium. The mutated ENaC subunit forms include fragments, sequences encoding ENaC subunits which are at least 80%, more preferably at least 90%, and still more preferably at least 95%, 96%, 97%, 98% or 99% identical at the protein level to the ENaC protein subunit sequences contain in SEQ ID NO: 2, 4, 6 and 8. These cells may further be engineered to express other sequences, e.g., taste GPCRs, i.e., T1Rs or T2Rs such as are described in other patent applications by the present Assignee Senomyx. The oocyte system is advantageous as it allows for direct injection of multiple mRNA species, provides for high protein expression and can accommodate the deleterious effects inherent in the overexpression of ENaC. The drawbacks are however that electrophysiological screening using amphibian oocytes is not as amenable to high throughput screening of large numbers of compounds and is not a mammalian system. As noted, the present invention embraces human delta beta gamma and human alpha beta gamma ENaC assays using mammalian cells and oocytes, preferably high throughput assays.

ENaC proteins are known to form heteromeric channels comprised of three subunits, an alpha, beta, and a gamma or delta subunit. The sequences of these respective ENaC subunits are disclosed in an earlier patent application by the present Assignee, U.S. Ser. No. 10/133,573 which is incorporated by reference in its entirety herein. Additionally, the sequences for these respective subunits are contained in the Sequence Listing that immediately precedes the claims of the subject application. Upon co-expression in a suitable cell these subunits result in a heterotrimeric channel having ion channel cation channel activity; in particular it responds to sodium and should similarly respond to lithium ions in cell-based assays such as those which are disclosed herein and in Senomyx' prior application referenced above.

Also different splice variants of these ENaC subunit sequences are known.

The ENaC channel has relatively high permeability to sodium and lithium and is amiloride-sensitive. Channel activity can be effectively measured, e.g., by recording ligand-induced changes in [$Na^+$] and measuring sodium or lithium ion influx using fluorescent ion-indicator dyes and fluorimetric imaging. ENaC is expressed in a number of epithelial tissues, including taste buds. Additionally, ENaC function is involved in kidney, lung function, blood pressure regulation et al. as disclosed above. Consequently, compounds identified as ENaC modulators have significant potential human therapeutic applications.

The Senomyx application incorporated by reference provides high throughput screening assays using mammalian cells transfected or seeded into wells or culture plates wherein functional expression in the presence of test compounds is allowed to proceed and activity is detected using membrane-potential fluorescent or ion (sodium) fluorescent dyes.

As discussed above, the invention specifically provides improved methods of screening for modulators, e.g., activators, inhibitors, stimulators, enhancers, etc., of human alpha or delta ENaC nucleic acids and proteins, using the human ENaC nucleic acid sequences provided herein. Such modulators can affect ENaC activity, e.g., by modulating ENaC transcription, translation, mRNA or protein stability; by altering the interaction of ENaC with the plasma membrane, or other molecules; or by affecting ENaC protein activity. Compounds are screened, e.g., using high throughput screening (HTS), to identify those compounds that can bind to and/or modulate the activity of a ENaC polypeptide or fragment thereof. In the present invention, ENaC proteins are recombinantly expressed in cells, e.g., human cells, or frog oocytes and the modulation of ENaC is assayed by using any measure of ion channel function, such as measurement of the membrane potential, or measures of changes in intracellular sodium or lithium levels. Methods of assaying ion, e.g., cation, channel function include, for example, patch clamp techniques, two electrode voltage clamping, measurement of whole cell currents, and fluorescent imaging techniques that use ion-sensitive fluorescent dyes and ion flux assays, e.g., radiolabeled-ion flux assays or ion flux assays.

A human delta ENaC enhancer identified as set forth in the current application can be used for a number of different purposes. For example, an ENaC enhancer can be included as a flavoring agent to modulate the umami or salty taste of foods, beverages, soups, medicines, and other products for human consumption. The compounds additionally can be used in vivo to treat disease conditions or physiological processes involving ENaC function. These applications include regulation of blood pressure, especially hypotension involving ENaC function, salt-wasting and the symptoms thereof including hyponatremia, hyperkalemia, dehydration, elevated serum aldosterone, and mineralcorticoid responsiveness, lung function especially in treatment of respiratory distress syndrome or pulmonary edema, to increase lung fluid absorption attributable to ENaC and to modulate extracellular volume and/or electrolyte homeostasis in individuals with normal or aberrant ENaC activity. In addition these conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract. In addition these conditions include pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system. These compounds potentially may be used to suppress or induce hunger or to modulate digestion in subjects in need thereof. Also compounds which modulate delta ENaC may be used to regulate umami taste cell development, apoptosis and/or signaling to nerve fibers. Also compounds which modulate delta ENaC activity may be used to treat or prevent cancers or malignancies associated with the digestive system such as by way of example cancers of the tongue, oral cavity, stomach, esophagus, small or large intestine, anus, pancreas, gall bladder, liver, or colon. Further compounds which modulate delta ENaC may be used to treat or prevent other gastrointestinal and metabolic diseases and conditions involving delta ENaC function such as described infra.

Additionally, the invention provides kits for carrying out the herein-disclosed assays.

DEFINITIONS

An ENaC associated biological function condition preferably refers to human umami salty taste perception. Additionally, ENaC associated functions may include conditions or diseases wherein modulation of ENaC function, preferably enhancement, is therapeutically beneficial. Such conditions include by way of example these conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract. In addition these conditions include pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. In addition these conditions include autoimmune or inflammatory diseases affecting the digestive system. These conditions further include digestive and hunger related conditions such as bulimia, obesity, diabetes, et al. as ENaC modulators may be used to suppress or induce hunger or to modulate digestion in subjects in need thereof. Also delta ENaC may regulate umami taste cell development, apoptosis and/or signaling to nerve fibers. Also compounds which modulate delta ENaC activity may be used to treat or prevent cancers or malignancies associated with the digestive system such as by way of example cancers of the tongue, oral cavity, stomach, esophagus, small or large intestine, anus, pancreas, gall bladder, liver, or colon. Further compounds which modulate delta ENaC may be used to treat or prevent other gastrointestinal and metabolic diseases and conditions involving delta ENaC function such as are described infra. Further compounds which modulate delta ENaC potentially may be used to regulate blood pressure, airway fluid reabsorption, salty taste, and renal electrolyte homeostasis and lung disorders and promotion of lung function in individuals in need of such treatment e.g., in respiratory distress syndrome and pulmonary edema.

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" is a polypeptide monomer that is an auxiliary subunit of a cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region. The ENaC beta subunit is contained in SEQ ID NO:4.

The term "authentic" or "wild-type" or "native" human ENaC nucleic acid sequences refer to the wild-type and mutant alpha, beta, gamma and delta nucleic acid sequences contained in the Sequence Listing that immediately precedes the claims as well as splice variants and other ENaC nucleic acid sequences generally known in the art.

The term "authentic" or "wild-type" or "native" human ENaC polypeptides refers to the polypeptide sequence contained in SEQ ID NO:2, 4, 6 and 8.

The term "modified hENaC nuclear acid sequence" or "optimized hENaC nucleic acid sequence" refers to a hENaC nucleic acid sequence which contains one or mutation that, e.g., those that affect (inhibit or enhance) ENaC activity in recombinant host cells, and most especially human cells such as HEK-293 cells or amphibian oocytes. Particularly, these mutations include those that affect gating by the resultant ENaC channel containing the mutated subunit sequence. The ENaC may comprise such mutations in one or several of the three subunits that constitute the ENaC. Further the invention may use ENaC subunit sequences which may be modified to introduce host cell preferred codons, particularly amphibian or human host cell preferred codons. Exemplary modified hENaC nucleic acid sequences which are useful in assays according to the invention are used in the examples.

The term "ENaC" protein or fragment thereof, or a nucleic acid encoding "ENaC" or a fragment thereof refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a ENaC nucleic acid or amino acid sequence of a ENaC protein, e.g., the ENaC subunit proteins encoded by the ENaC nucleic acid sequences contained in the Sequence Listing that precedes the claims of this application as well as fragments thereof, and conservatively modified variants thereof; (3) polypeptides encoded by nucleic acid sequences which specifically hybridize under stringent hybridization conditions to an anti-sense strand corresponding to a nucleic acid sequence encoding a ENaC protein subunit, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a ENaC nucleic acid, e.g., those disclosed herein.

An ENaC polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention preferably use naturally occurring or recombinant human ENaC molecules. ENaC proteins typically have ion channel activity, i.e., they are permeable to sodium or lithium.

By "determining the functional effect" or "determining the effect on the cell" is meant assaying the effect of a compound that increases or decreases a parameter that is indirectly or directly under the influence of a ENaC polypeptide e.g., functional, physical, phenotypic, and chemical effects. Such functional effects include, but are not limited to, changes in ion flux, membrane potential, current amplitude, and voltage gating, a as well as other biological effects such as changes in gene expression of ENaC or of any marker genes, and the like. The ion flux can include any ion that passes through the channel, e.g., sodium or lithium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties.

"Inhibitors," "activators," and "modulators" of ENaC polynucleotide and polypeptide sequences are used to refer to activating, inhibitory, or modulating molecules identified using in vitro and in vivo assays of ENaC polynucleotide and polypeptide sequences. Inhibitors are compounds that; e.g., bind to, partially or totally block activity, decrease, prevent, delay activation, inactivate, desensitize, or down regulate the activity or expression of ENaC proteins, e.g., antagonists. "Activators" are compounds that increase, open, activate, facilitate, enhance activation, sensitize, agonize, or up regulate ENaC protein activity. Inhibitors, activators, or modulators also include genetically modified versions of ENaC proteins, e.g., versions with altered activity, as well as naturally occurring and synthetic ligands, antagonists, agonists, peptides, cyclic peptides, nucleic acids, antibodies, antisense molecules, siRNA, ribozymes, small organic molecules and the like. Such assays for inhibitors and activators include, e.g., expressing ENaC protein in vitro, in cells, cell extracts, or cell membranes, applying putative modulator compounds, and then determining the functional effects on activity, as described above.

Samples or assays comprising ENaC proteins that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of ENaC is achieved when the activity value relative to the control is about 80%, preferably 50%, more preferably 25-0%. Activation of ENaC is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic compound, preferably a small molecule, or a protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, siRNA, oligonucleotide, ribozyme, etc., to be tested for the capacity to modulate cold sensation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., ENaC nucleotide sequences contained in the Sequence Listing), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nucl. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci., USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of .beta.-sheet and .alpha.-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2.times. SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1.times. SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The term antibody, as used herein, also includes antibody fragments either produced by the modification of whole antibodies, or those synthesized de novo using recombinant DNA methodologies (e.g., single chain Fv), chimeric, humanized or those identified using phage display libraries (see, e.g., McCafferty et al., Nature 348:552-554 (1990)) For preparation of antibodies, e.g., recombinant, monoclonal, or polyclonal antibodies, many technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988) and Harlow & Lane, Using Antibodies, A Laboratory Manual (1999); and Goding, Monoclonal Antibodies: Principles and Practice (2d ed. 1986)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to ENaC protein, polymorphic variants, alleles, orthologs, and conservatively modified variants, or splice variants, or portions thereof, can be selected to obtain only those polyclonal antibodies that are specifically immunoreactive with ENaC proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

Recombinant Expression of ENaC

To obtain high level expression of a cloned gene, such as those cDNAs encoding ENaC, one typically subclones ENaC into an expression vector that contains a strong promoter to direct transcription, a transcription/translation terminator, and if for a nucleic acid encoding a protein, a ribosome binding site for translational initiation. Suitable eukaryotic and prokaryotic promoters are well known in the art and described, e.g., in Sambrook et al., and Ausubel et al., supra. For example, bacterial expression systems for expressing the ENaC protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. For example, retroviral expression systems may be used in the present invention. As described infra, the subject modified hENaC is preferably expressed in human cells such as HEK293 cells which are widely used for high throughput screening.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the ENaC-encoding nucleic acid in host cells. A typical expression cassette thus contains a promoter operably linked to the nucleic acid sequence encoding ENaC and signals required for efficient polyadenylation of the transcript, ribosome binding sites, and translation termination. Additional elements of the cassette may include enhancers and, if genomic DNA is used as the structural gene, introns with functional splice donor and acceptor sites. As noted previously, the exemplified modified hENaC is modified to remove putative cryptic splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

The vectors used in the invention may include a regulatable promoter, e.g., tet-regulated systems and the RU486 system (see, e.g., Gossen & Bujard, Proc. Nat'l Acad. Sci. USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a ENaC encoding sequence under the direction of the polyhedrin promoter or other strong baculovirus promoters.

The elements that are typically included in expression vectors also include a replicon that functions in the particular host cell. In the case of *E. coli*, the vector may contain a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods may be used to produce bacterial, mammalian, yeast or insect cell lines that express large quantities of ENaC protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ENaC.

After the expression vector is introduced into the cells, the transfected cells are cultured under conditions favoring expression of ENaC. In some instances, such ENaC polypeptides may be recovered from the culture using standard techniques identified below.

Assays for Modulators of ENaC Protein

Modulation of an ENaC protein can be assessed using a variety of in vitro and in vivo assays, including cell-based models as described above. Such assays can be used to test for inhibitors and activators of ENaC protein or fragments thereof, and, consequently, inhibitors and activators of ENaC. Such modulators of ENaC protein are useful in medications or as flavorings to modulate ENaC associated umami or salty taste, or treating disorders related to ENaC function. Modulators of ENaC protein herein may be capable of opening mutant ENaC channels with reduced sodium-transport capacity and in treating gastrointestinal and metabolic functions involving delta ENaC activity.

As noted above, the ENaC protein used in the subject cell based assays will preferably be encoded by hENaC nucleic acid sequences encoding subunits that care contained in FIGS. 8-11. Alternatively, these sequences may be modified to comprise at least one mutation which affects (reduces or enhances) ENaC function relative to the corresponding wild-type ENaC as the assays preferably screen for compounds (enhancers) capable of "restoring" the function thereof in specific cells, preferably frog oocytes or mammalian cells, preferably human cells.

Compounds identified in such assays will then be evaluated in vivo to confirm that this affect on ENaC is obtained in vivo and consequently that the identified compound is suitable for correcting or modulating a function involving ENaC such as those afore-identified. Assays using cells expressing ENaC proteins, either recombinant or naturally occurring, can be performed using a variety of assays, in vitro, in vivo, and ex vivo, as described herein. To identify molecules capable of modulating ENaC, assays are performed to detect the effect of various candidate modulators on ENaC activity preferably a mutant ENaC in a cell.

The channel activity of ENaC proteins can be assayed using a variety of assays to measure changes in ion fluxes including patch clamp techniques, measurement of whole cell currents, radiolabeled ion flux assays or a flux assay coupled to atomic absorption spectroscopy, and fluorescence assays using voltage-sensitive dyes or lithium or sodium sensitive dyes (see, e.g., Vestergarrd-Bogind et al., J. Membrane Biol. 88:67-75 (1988); Daniel et al., J. Pharmacol. Meth. 25:185-193 (1991); Hoevinsky et al., J. Membrane Biol. 137:59-70 (1994)). For example, a nucleic acid encoding an ENaC protein or homolog thereof can be injected into *Xenopus oocytes* or transfected into mammalian cells, preferably human cells such as HEK293 cells. Channel activity can then be assessed by measuring changes in membrane polarization, i.e., changes in membrane potential.

A preferred means to obtain electrophysiological measurements is by measuring currents using patch clamp techniques, e.g., the "cell-attached" mode, the "inside-out" mode, and the "whole cell" mode (see, e.g., Ackerman et al., New Engl. J. Med. 336:1575-1595, 1997). Whole cell currents can be determined using standard methodology such as that described by Hamil et al., Pflugers. Archiv. 391:185 (1981).

Channel activity is also conveniently assessed by measuring changes in intracellular ion levels, i.e., sodium or lithium. Such methods are exemplified herein. For example, sodium flux can be measured by assessment of the uptake of radiolabeled sodium or by using suitable fluorescent dyes. In a typical microfluorimetry assay, a dye which undergoes a change in fluorescence upon binding a single sodium ion, is loaded into the cytosol of ENaC-expressing cells. Upon exposure to ENaC agonist, an increase in cytosolic sodium is reflected by a change in fluorescence that occurs when sodium is bound.

The activity of ENaC polypeptides can in addition to these preferred methods also be assessed using a variety of other in vitro and in vivo assays to determine functional, chemical, and physical effects, e.g., measuring the binding of ENaC to other molecules, including peptides, small organic molecules, and lipids; measuring ENaC protein and/or RNA levels, or measuring other aspects of ENaC polypeptides, e.g., transcription levels, or physiological changes that affects ENaC activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors of KCNB proteins. Modulators thus identified are useful for, e.g., many diagnostic and therapeutic applications.

In Vitro Assays

Assays to identify compounds with ENaC modulating activity are preferably performed in vitro. The assays herein preferably use full length ENaC subunit proteins or a variant thereof. This protein can optionally be fused to a heterologous protein to form a chimera. In the assays exemplified herein, cells which express the full-length ENaC polypeptide are used in high throughput assays are used to identify compounds that modulate wild-type and mutant ENaCs. Alternatively, purified recombinant or naturally occurring ENaC protein can be used in the in vitro methods of the invention. In addition to purified ENaC protein or fragment thereof, the recombinant or naturally occurring ENaC protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands such as menthol). The in vitro assays include measuring changes in spectroscopic (e.g., fluorescence, absorbance, refractive index), hydrodynamic (e.g., shape), chromatographic, or solubility properties for the protein.

Preferably, a high throughput binding assay is performed in which the ENaC protein is contacted with a potential modulator and incubated for a suitable amount of time. A wide variety of modulators can be used, as described below, including small organic molecules, peptides, antibodies, and ENaC ligand analogs. A wide variety of assays can be used to identify ENaC-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for the ENaC family are known. Also amiloride and phenamil are known to inhibit ENaC function. In such assays the known ligand is bound first, and then the desired compound i.e., putative enhancer is added. After the ENaC protein is washed, interference with binding, either of the potential modulator or of the known ligand, is determined. Often, either the potential modulator or the known ligand is labeled.

In addition, high throughput functional genomics assays can also be used to identify modulators of cold sensation by identifying compounds that disrupt protein interactions between ENaC and other proteins to which it binds. Such assays can, e.g., monitor changes in cell surface marker expression, changes in intracellular calcium, or changes in membrane currents using either cell lines or primary cells. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the ENaC protein encoded by the cDNA can be isolated using a yeast two-hybrid system, mammalian two hybrid system, or phage display screen, etc. Targets so identified can be further used as bait in these assays to identify additional components that may interact with the ENaC channel which members are also targets for drug development (see, e.g., Fields et al., Nature 340:245 (1989); Vasavada et al., Proc. Nat'l Acad. Sci. USA 88:10686 (1991); Fearon et al., Proc. Nat'l Acad. Sci. USA 89:7958 (1992); Dang et al., Mol. Cell. Biol. 11:954 (1991); Chien et al., Proc. Nat'l Acad. Sci. USA 9578 (1991); and U.S. Pat. Nos. 5,283,173, 5,667,973, 5,468,614, 5,525,490, and 5,637,463).

Cell-Based Assays

In preferred embodiments, wild-type and mutant ENaC subunit proteins are expressed in a cell, and functional, e.g., physical and chemical or phenotypic, changes are assayed to identify ENaC modulators that modulate ENaC function or which restore the function of mutant ENaCs, e.g., those having impaired gating function. Cells expressing ENaC proteins can also be used in binding assays. Any suitable functional effect can be measured, as described herein. For example, changes in membrane potential, changes in intracellular lithium or sodium levels, and ligand binding are all suitable assays to identify potential modulators using a cell based system. Suitable cells for such cell based assays include both primary cells and recombinant cell lines engineered to express an ENaC protein. The ENaC proteins therefore can be naturally occurring or recombinant. Also, as described above, fragments of ENaC proteins or chimeras with ion channel activity can be used in cell based assays. For example, a transmembrane domain of an ENaC protein can be fused to a cytoplasmic domain of a heterologous protein, preferably a heterologous ion channel protein. Such a chimeric protein would have ion channel activity and could be used in cell based assays of the invention. In another embodiment, a domain of the ENaC protein, such as the extracellular or cytoplasmic domain, is used in the cell-based assays of the invention.

In another embodiment, cellular ENaC polypeptide levels can be determined by measuring the level of protein or mRNA. The level of ENaC protein or proteins related to ENaC ion channel activation are measured using immunoassays such as western blotting, ELISA and the like with an antibody that selectively binds to the ENaC polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, ENaC expression can be measured using a reporter gene system. Such a system can be devised using an ENaC protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, Nature Biotechnology 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to signal transduction can be measured. An activated or inhibited ENaC will alter the properties of target enzymes, second messengers, channels, and other effector proteins. The examples include the activation of phospholipase C and other signaling systems. Downstream consequences can also be examined such as generation of diacyl glycerol and IP3 by phospholipase C.

Assays for ENaC activity include cells that are loaded with ion or voltage sensitive dyes to report activity, e.g., by observing sodium influx or intracellular sodium release. Assays for determining activity of such receptors can also use known agonists and antagonists for ENaC receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. Radiolabeled ion flux assays or a flux assay coupled to atomic absorption spectroscopy can also be used.

Animal Models

Animal models also find potential use in screening for modulators of ENaC activity. Similarly, transgenic animal technology including gene knockout technology, for example as a result of homologous recombination with an appropriate gene targeting vector, or gene overexpression, will result in the absence or increased expression of the ENaC protein. The same technology can also be applied to make knock-out cells. When desired, tissue-specific expression or knockout of the ENaC protein may be necessary. Transgenic animals generated by such methods find use as animal models of ENaC related responses.

Knock-out cells and transgenic mice can be made by insertion of a marker gene or other heterologous gene into an endogenous ENaC gene site in the mouse genome via homologous recombination. Such mice can also be made by substituting an endogenous ENaC with a mutated version of the ENaC gene, or by mutating an endogenous ENaC, e.g., by exposure to known mutagens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., Science 244:1288 (1989)). Chimeric targeted mice can be derived according to Hogan et al., Manipulating the Mouse Embryo: A Laboratory Manual (1988) and Teratocarcinomas and Embryonic Stem Cells: A Practical Approach (Robertson, ed., 1987).

Candidate ENaC Modulators

The compounds tested as modulators of ENaC protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an ENaC protein. Typically, test compounds will be small organic molecules, peptides, lipids, and lipid analogs. In one embodiment, the compound is a menthol analog, either naturally occurring or synthetic.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md.). C. Solid State and Soluble High Throughput Assays Additionally soluble assays can be effected using a ENaC protein, or a cell or tissue expressing a ENaC protein, either naturally occurring or recombinant. Still alternatively, solid phase based in vitro assays in a high throughput format can be effected, where the ENaC protein or fragment thereof, such as the cytoplasmic domain, is attached to a solid phase substrate. Any one of the assays described herein can be adapted for high throughput screening, e.g., ligand binding, calcium flux, change in membrane potential, etc.

In the high throughput assays of the invention, either soluble or solid state, it is possible to screen several thousand different modulators or ligands in a single day. This methodology can be used for ENaC proteins in vitro, or for cell-based or membrane-based assays comprising an ENaC protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book 1 (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of, e.g., peptides); Geysen et al., J. Immunol. Meth. 102:259-274 (1987) (describing synthesis of solid phase components on pins); Frank & Doring, Tetrahedron 44:6031-6040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753-759 (1996) (all describing arrays of biopolymers fixed to solid substrates). Non-chemical approaches for fixing tag binders to substrates include other common methods, such as heat, cross-linking by UV radiation, and the like.

Having described the invention supra, the following examples provide the further illustration of some preferred embodiments of the invention. These examples are provided only for purposes of illustration and should not be construed as limiting the subject invention.

EXAMPLE 1

In this experiment HEK293 cells which were transfected with sequences encoding the human alpha, beta and gamma subunits were used to screen for the effect of amiloride on NaCl induced changes in membrane potential. The results of this experiment are contained in FIG. 1 (Panels A and B): As shown in Panel A amiloride totally inhibited the NaCl induced changes in membrane potential in the HE 293 cells expressing the alpha ENaC channel. These HEK293 cells were transiently transfected with plasmids containing the alpha, beta and gamma ENaC encoding nucleic acid sequences and then loaded with a membrane potential dye (FMP; Molecular Devices) in the absence of sodium (NaCl was replaced with NMDG) at room temperature for one hour. Cells were then stimulated with 70 mM NaCl with (red trace) or without (white trace) 6.25 micromolar amiloride. Changes in membrane potential (fluorescent signal) in HEK293 cells were monitored on a FLIPR system (Molecular Devices). The experiment in Panel B shows that amiloride totally inhibited the NaCl induced change in membrane potential in HEK293 cells expressing the deltaENaC channel. HEK293 cells were transiently transfected with the gamma, beta, and delta subunit containing plasmids and were loaded with a membrane potential dye (FMP; Molecular Devices) in the absence of sodium (NaCl was replaced with NMDG) at room temperature for one hour. Cells were then stimulated with 70 mM NaCl with (red trace) or without (white trace) 50 micromolar amiloride. Changes in membrane potential (fluorescent signal) were monitored on a FLIPR system (Molecular Devices). In the experiment in Panel C it can be seen that amiloride is more potent at inhibiting alphaENaC than deltaENaC. Therein cells were prepared and treated as in Panels A and B. Increasing concentrations of amiloride were used to assess potency at inhibiting the different forms of ENaC. The results also show that HEK-293 cells which are not transfected with ENaC plasmids (HEK) do not show any change in membrane potential upon NaCl add back under the same experimental conditions.

EXAMPLE 2

This example relates to the fluorescent experiments contained in FIG. 2, Panels A, B and C. In the experiment in Panel A it can be seen that the enhancer S559 increases the NaCl-induced change in membrane potential in HEK293 cells expressing the alphaENaC channel. HEK293 cells were transiently transfected with plasmids containing sequences encoding the human alpha, beta, and gamma ENaC subunits and were loaded with a membrane potential dye (FMP; Molecular Devices) in the absence of sodium (NaCl was replaced with NMDG) at room temperature for one hour. Cells were then stimulated with 17.5 mM NaCl with (red trace) and without (white trace) 15 micromolar S559. Changes in membrane potential (fluorescent signal) were monitored on a FLIPR system (Molecular Devices). Under these conditions, S559 increased the NaCl-induced change in membrane potential by 2.5 fold indicating enhancement of alphaENaC (Panel C). In Panel B the experiment contained therein reveals that dye loading in the presence of NaCl and stimulation with a greater NaCl concentration improves the S559 enhancement effect. HEK293 cells were transiently transfected with the alpha, beta and gamma ENaC subunit plasmids and were loaded with a membrane potential dye (FMP; Molecular Devices) in the presence of 140 mM NaCl at room temperature for one hour. Cells were stimulated with 140 mM NaCl with or without 15 micromolar S559 as indicated on the graph. Changes in membrane potential (Fluorescent signal) were monitored on a FLIPR system (Molecular Devices). Under these conditions, S559 increased the NaCl-induced change in membrane potential by 17.6 fold (Panel C).

EXAMPLE 3

This example relates to the experiments contained in FIG. 3, Panels A and B. The experiment in Panel A shows that the effects of the alphaENaC enhancer S559 are blocked by amiloride. In the experiment HEK293 cells again transfected transiently with plasmids containing the alpha, beta, and gamma ENaC subunit nucleic acid sequences and were treated as described in Example 2., Panel B (Protocol 2). Changes in membrane potential (fluorescent signal) were monitored on a FLIPR system (Molecular Devices). Under these conditions, 3 micromolar amiloride almost totally abolishes S559 effects indicating that S559 enhances alphaENaC and not any other current in HEK293 cells. In the experiment in Panel B it can be seen that cells which do not express alphaENaC do not exhibit any effect of S559 or amiloride. HEK293 cells were transfected with a mock plasmid (pUC19) and treated as described above. Changes in membrane potential (fluorescent signal) were monitored on a FLIPR system (Molecular Devices).

EXAMPLE 4

This example relates to the experiment contained in FIG. 4. This experiment illustrates the robustness of the screening conditions developed for alphaENaC. HEK293 cells were transiently transfected with plasmids containing nucleic acid sequences encoding the alpha, beta and gamma ENaC subunits and were treated as described in FIG. 2; Panel B (Protocol 2). A 384 well plate containing screening compounds was used to stimulate the transfected cells in the FLIPR. 10 wells of the compounds plate were spiked randomly with S559 at 15 micromolar. The results clearly show that all the spiked wells (circled) display fluorescence counts (F) that are well above the statistical cutoff (dotted line). These results indicate that these assay conditions can allow for the detection of alphaENaC enhancers in more than 95% of the time, in screening mode. The arrows indicate internal controls used in the screening plate.

EXAMPLE 5

This example relates to the experiment in FIG. 5. It can be seen therefrom that the improved assay conditions of the invention allow for the discovery of novel alphaENaC enhancers. In this experiment HEK293 cells were transfected transiently with plasmids containing nucleic acid sequences encoding the alpha, beta, and gamma ENaC subunits and were treated as described in FIG. 2, Panel B (Protocol 2). Thereafter 15,000 compounds at a concentration of 10 micromolar were tested on FLIPR using a similar plate layout as in FIG. 4. Hits above the 25% cut off activity value level were then submitted for conformation testing using current measurements in oocytes expressing the alphaENaC channel. It was shown that the compound S818 showed reproducible activity in FLIPR and oocyte assays, displaying a similar potency at enhancing alphaENaC.

EXAMPLE 6

This example relates to the experiments contained in FIG. 6, Panels A and B. The example shows the assay conditions developed to screen for deltaENaC enhancers. In the experiment HEK293 cells were transiently transfected with the delta, beta, and gamma ENaC subunit plasmids and were treated as described in FIG. 2; panel B (Protocols 1 and 2). Panel A shows the results of a screening plate using protocol 1. In this particular case, cells were loaded with the membrane potential dye in NMDG and compounds were added to the cells in 7 mM NaCl (instead of the 17.5 mM NaCl typically used for alphaENaC expressing cells). The 70 mM NaCl control represents the maximum level of deltaENaC stimulation measurable in this assay. The experiment in Panel B shows the results of a screening plate using protocol 2. In this particular case, cells were loaded with membrane potential dye in 140 mM NaCl and compounds were added to the cells in 140 mM NaCl. In this assay, the high control value is obtained with cells loaded in NMDG and stimulated with 140 mM NaCl. This control insures that the cells express a functional deltaENaC channel. The circled triangles correspond to the primary hits.

EXAMPLE 7

This example relates to the experiments contained in FIG. 7, Panels A and B. It shows the identification of deltaENaC enhancers using the subject novel and improved screening assay conditions. HEK293 cells transiently transfected with plasmids containing nucleic acid sequences encoding the human delta, beta and gamma ENaC subunits and were treated as described in FIG. 2; Panel B (Protocol 2). The left panel shows that, in cells expressing deltaENaC, S16332280 induces a dose dependent change in membrane potential, indicating deltaENaC enhancement under these conditions. The same compound did not have any effect on un-transfected HEK293 cells (Panel B).

EXAMPLE 8

Taste Cell Specific Expression of Delta ENaC in Primate Taste Cells

This experiment which is contained in FIG. 12 demonstrated taste-specific expression of delta ENaC in primate CV taste tissue by PCR screening. Primate PCR primers specific for primate genes were used to amplify cDNA from purified circumvallate (CV) taste or lingual cells. '+' indicates that reverse transcription was performed and cDNA was added to the PCR reaction; '−' indicates no reverse transcription was performed and no cDNA was added to the PCR reaction. Of the four ENaC genes, delta ENaC is only present in taste cells but not lingual cells.

EXAMPLE 9

Other double labeling in situ hybridization experiments were conducted with primate circumvallate papilla cells using immunohistochemistry labels that detected for delta ENaC and PKD1L3 expression therein. The results contained in FIG. 13 show that delta ENaC (purple color; left image) does not colocalize with PKD1L3 (red color; middle image) Rather, it can be seen from the figure that the purple and red colors label distinct cells in the merged image contained on the right side of the figure. This data therefore shows that Delta ENaC is not expressed in primate taste cells that express PKD1L3 (primate circumvallate cells which cells are believed to be involved in sour taste perception). The results were validated as the figure contains data for 2 experiments (top and bottom sets of images) with similar results being obtained in both experiments.

EXAMPLE 10

Other in situ double labeling hybridization experiments were conducted using immunohistochemistry labels that detected for Delta ENaC and TRPM5 expression on primate circumvallate papilla cells. The results contained in FIG. 14 revealed that Delta ENaC (purple color; left image) is expressed in a subset of TRPM5 cells (red color; middle image). It can be seen from the figure that the purple color is always associated with a red color in the merged image contained on the right side of the figure. These data reveal that Delta ENaC is expressed in a subset of TRPM5 cells. The figure contains results for three experiments (top, middle, and bottom sets of images).

EXAMPLE 11

Other double labeling in situ hybridization experiments were conducted using immunohistochemistry labels that detected for Alpha ENaC and PKD1L3 gene expression on primate circumvallate cells. The results contained in FIG. 15 reveal that Alpha ENaC (purple color; left image) is present in cells expressing PKD1L3 (red color; middle image). The results in the figure indicate that the red color is always associated with a purple color in the merged image contained on the right side of the figure. These data therefore show that alpha ENaC is expressed in sour cells. Two primate taste buds are shown in this figure.

EXAMPLE 12

Other in situ double labeling hybridization experiments were conducted using immunohistochemistry labels that detected for alpha ENaC and TRPM5 expression on primate circumvallate cells. The results of these experiments are contained in FIG. 16. The data reveal that alpha ENaC (purple color; left image) is present in cells expressing TRPM5 (red color; middle image). It can be seen therefrom that the red color is always associated with a purple color in the merged image on the right side of the figure. These data reveal that alpha ENaC is expressed in sweet, bitter, and umami taste specific cells. Two primate taste buds are shown in the figure.

EXAMPLE 13

Delta ENaC is Expressed in T1R1 Umami Cells

Double label in situ hybridization of primate circumvallate papilla were conducted contained in FIG. 17 showing that Delta ENaC (purple color; left image) colocalizes with T1R1 (red; middle image). It can be seen therein that Delta ENaC cells express T1R1, a marker of umami cells (merged image on the right). However, not all T1R1 cells express Delta ENaC. Therefore, the results indicate that Delta ENaC labels and is expressed in a subset of umami cells. Two examples are shown (top and bottom sets of images). Quantitation of labeled taste cells revealed that Delta ENaC is expressed in 40-50% of umami T1R1 cells.

EXAMPLE 14

Delta ENAC is not Expressed in T1R2 Sweet Cells

Additional double label in situ hybridization experiments using primate circumvallate papilla were conducted. These results contained in FIG. 18 show that Delta ENaC (purple color; left image) does not colocalize with T1R2 (red; middle image). It can be therein that the purple and red colors label different cells in the merged image on the right. T1R2 is a marker of sweet cells Delta ENaC generally is not in sweet cells. Two examples are shown in FIG. 18 (top and bottom sets of images).

EXAMPLE 15

Delta ENAC is Only Expressed in Some T1R3 Cells

Further double label in situ hybridization of primate circumvallate papilla were conducted. These results contained in FIG. 19 reveal that Delta ENaC (purple color; left image) colocalizes with some T1R3 cells (red; middle image). It can be seen from the results in the Figure that every Delta ENaC cell (purple) colocalizes with a T1R3 cell (red), but that every T1R3 cell does not colocalize with a Delta ENaC cell in the merged image on the right. T1R3 is a marker of sweet and umami cells. Taken together with data that Delta ENaC colocalizes with T1R1 but not significantly with T1R2, these results indicate that T1R3 cells that colocalize with Delta ENaC would be T1R1 umami cells whereas T1R3 cells that do not colocalize with Delta ENaC would largely be T1R2 sweet cells. Two examples are shown (top and bottom sets of images).

EXAMPLE 16

Delta ENaC is not Expressed in T2R Bitter Cells

Figure 20:
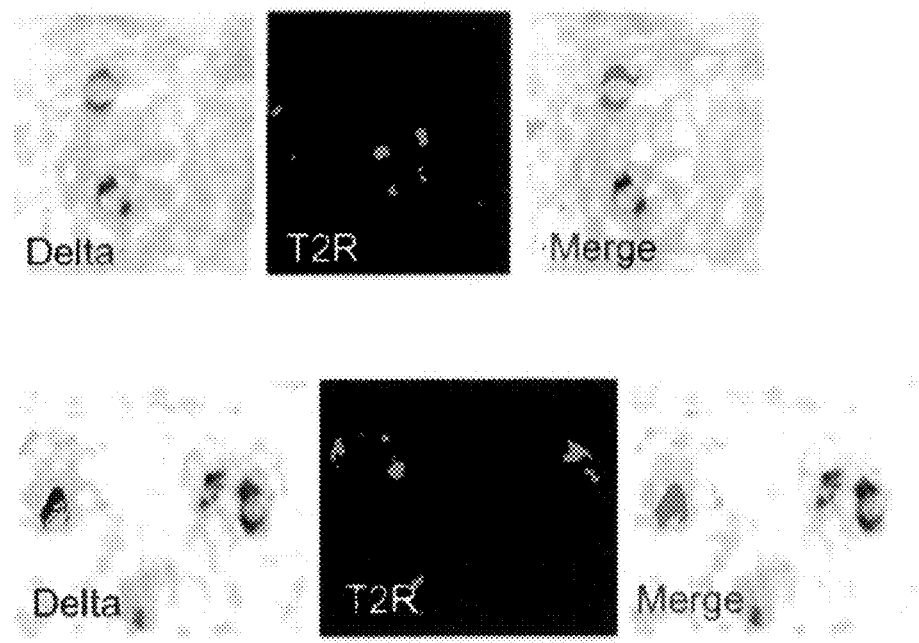
FIG. 20 contains in situ hybridization experiments in primate circumvallate cells showing that delta ENaC is not expressed in T2R bitter taste cells.

Further double label in situ hybridization of primate circumvallate papilla were conducted. These results contained in FIG. 20 reveal that Delta ENaC (purple color; left image) does not colocalize with T2R5 (red; middle image). Note that purple and red colors label different cells in the merged image on the right. T2R5 are markers of bitter cells and Delta ENaC is not in bitter cells. Two examples are shown (top and bottom sets of images).

CONCLUSIONS AND OBSERVATIONS BASED ON EXPERIMENTAL RESULTS

The results above relating to the histological expression of delta ENaC in primate (monkey) taste receptor cells and double labeling in situ hybridization experiments provide the basis for a number of reasonable conclusions.

For example the results show that delta ENaC is expressed in specific taste cell subtypes including T1R1 taste cells. Experiments were performed to determine what specific taste cell type(s) the Delta ENaC pore forming sodium channel subunit was expressed in. The results described supra demonstrated that Delta ENaC was expressed in a subset of cells expressing TRPM5, a marker of sweet, bitter, and umami taste cells, but not in cells expressing PKD2L1/PKD1l, markers of sour cells.

Also, these experiments revealed that Delta ENaC is specifically expressed in a subset of umami cells expressing the umami receptor T1R1. The expression of Delta ENaC in a subset of T1R1 umami cells suggests that Delta ENaC can selectively regulate the biology of umami taste cells, including but not limited to umami taste perception, umami taste cell development and apoptosis, and umami cell signaling to nerve fibers. In addition, salt (sodium from the umami tastant monosodium glutamate) flowing through Delta ENaC in umami cells may contribute to the sensation of umami taste. Accordingly, Delta ENaC may be a ancillary umami receptor component.

1) Therefore Delta ENaC is a marker of a subset of umami cells. These cells may be mature and capable of umami taste or immature/senescent and not capable of umami taste.
2) Also the results suggest that Delta ENaC, and compounds that enhance or inhibit Delta ENaC, can selectively modulate umami taste cell function and responses to umami tastants.
3) Further the results suggest that Delta ENaC, and compounds that enhance or inhibit Delta ENaC, can modulate umami taste cell development and apoptosis.
4) Still further the results suggest that Delta ENaC is an ancillary umami receptor.
5) More specifically, the results suggest that salt, meaning sodium from the umami tastant monosodium glutamate, flowing through Delta ENaC in umami cells may contribute to the sensation of umami taste.
6) Moreover, the results suggest that Delta ENaC, and compounds that enhance or inhibit Delta ENaC, can modulate the function of any cell expressing the umami receptor, including but not limited to cells in the gastrointestinal tract such as enteroendocrine cells that regulate gastric motility and peptide secretion (e.g. GLP-1: glucagon-like peptide 1; GIP: gastric inhibitory peptide).
7) Alpha ENaC is expressed in sweet, bitter, umami, sour, and perhaps other taste cell types, suggesting that Alpha ENaC, and compounds that enhance or inhibit Alpha ENaC, can modulate sweet, bitter, umami, and sour taste cell function as well as sweet, bitter, umami, and sour taste. Small molecule activation of hENaC may have implications for human biology including blood pressure regulation, airway fluid reabsorption, salt taste, and renal electrolyte homeostasis. Additionally, the activation of hENaC may prove useful in increasing blood pressure in individuals with hypotension by increasing hENaC-dependent renal $Na^+$ reabsorption. Similarly, activation of hENaC in the apical membrane of distal airway epithelia could promote lung function in neonatal respiratory distress syndrome or pulmonary edema by increasing hENaC-dependent $Na^+$ and lung fluid absorption (Barker et al., J Appl Physiol. 93:1542-1548 (2002); and Hummler et al., Nat. Genet., 12:325-328 (1996).

Further, the activation of hENaC in taste papillae on the tongue may be involved in umami or salt taste sensation by promoting $Na^+$ transport into taste bud cells (Kretz et al., J Histochem Cytochem., 4751-64 (1999); Lin et al., J. Comp. Neurol. 405:406-420 (1999)). This has obvious consumer applications in improving the taste and palatability of low salt foods and beverages.

Moreover, the activation of residual hENaC function in individuals with PHA1 may be used to correct dehydration and salt wasting accompanying mineralocorticoid resistance (Zennaro et al., Trends Endocrinol. Metab. 15:264-270 (2004). Indeed, 6363969 rescued αβG37Sγ ENaC, a PHA1 mutant with compromised channel gating (Grunder et al., EMBO J 16:899907 (1997). This indicates that hENaC channel openers may be administered in vivo in situations where improved Na⁺ flux across epithelial membranes is clinically desirable. In conclusion, promoting hENaC-dependent Na⁺ and fluid transport across epithelial membranes may find utility in modulating extracellular volume and electrolyte homeostasis in both normal and diseased states.

REFERENCES

All the references cited in this application are incorporated by reference in their entirety herein.

SEQUENCE LISTING OF ENaC DNA AND PROTEIN SEQUENCES

The ENaC DNA and protein sequences for human alpha ENaC subunit, human beta ENaC subunit, human gamma ENaC subunit and human delta ENaC subunit are contained in FIGS. 8-11 which contain SEQ ID NOs 1 through 8 inclusive.

The invention claimed is:

1. A fluorescent assay method for identifying a compound that modulates delta Epithelial Sodium Channel (ENaC) or alpha ENaC activity comprising the following: (i) obtaining a test cell that expresses either a functional (sodium responsive) human delta ENaC channel comprised of the beta, gamma and delta subunit contained in SEQ ID NO: 4, SEQ ID NO:6 and SEQ ID NO:8, respectively, or (b) a functional (sodium responsive) human alpha ENaC channel comprised of the alpha, beta and gamma subunit polypeptides possessing at least 90% sequence identity to the polypeptides contained in SEQ ID NO:2, SEQ ID NO:4, and SEQ ID NO:6, respectively;

(ii) loading said test cell with an ion-sensitive dye or a membrane potential dye; (iii) contacting said dye-loaded test cell with at least 140 mM of sodium for at least 5 minutes and up to about an hour prior to contacting the dye-loaded test cell with a putative ENaC enhancer compound; (iv) after step (iii), contacting the dye-loaded test cell that has been contacted with at least 140 mM of sodium for at least 5 minutes and up to about an hour in the absence of the putative ENaC enhancer compound with a composition comprising a putative ENaC enhancer compound, with the proviso that there are no intervening steps between steps (iii) and (iv) that remove the sodium added to the dye-loaded test cell in step (iii);

(v) fluorometrically assaying sodium conductance of the sodium contacted dye-loaded test cell in the presence and absence of said putative ENaC enhancer compound, (vi) identifying the potential ENaC enhancer compound as a potential alpha ENaC enhancer or potential delta ENaC enhancer based on whether it increases or decreases sodium conductance; and (vii) testing the effect of said potential ENaC enhancer compound in a human taste test; wherein said sodium contacting step (iii) prior to the addition of the putative ENaC enhancer compound to the dye-loaded test cells in step (iv) improves the sensitivity of the assay by enhancing the signal-to-background ratio of potential ENaC enhancers compounds by at least 5-fold relative to the same screening assay in which the screened cells are contacted with no sodium prior to being screened against the putative ENaC enhancer compound.

2. The method of claim 1, wherein the screened cell expresses the human delta ENaC.

3. The method of claim 1, wherein the screened cell expresses the human alpha ENaC.

4. The method of claim 1, wherein said dye-loaded test cell is contacted in step (iii) for at least 30 minutes to an hour with said amount of sodium prior to being screened against a putative ENaC enhancer compound.

5. The method of any of claim 1, wherein the dye-loaded test cell is also contacted with sodium during step (iv).

6. The method of claim 1, wherein the dye-loaded test cell is a mammalian cell.

7. The method of claim 6, wherein said mammalian cell is a COS, BHK, CHO, NIH3T3, African Green Monkey, monkey L, Ltk or a Swiss3T3 cell.

8. The method of claim 1, wherein the test cell is an oocyte.

9. The method of claim 1, wherein said fluorimetric assay is a two electrode voltage clamping assay.

10. The method of claim 1, wherein said fluorimetric assay is a patch clamp assay.

11. The method of claim 1, wherein the membrane potential dye selected from the group consisting of pyridinium, 4-(2-(6-(dibutylamino)-2-naphthalen-yl)ethenyl)-1-(3-sulfopropyl)hydroxide, inner salt, (2)(bis-(1,2-dibabituric acid)-triethine oxanol, 1,2-dietradecanoyl-sn-glycerol-3phosphoethanolamine, triethylammonium salt and 1,3-benzenedicarboxylic acid, 4,4-[1,4,10-trioxa-7,13-diazacyclopentadecane-7,13-diylbis(5-methoxy-6,1,2-benzofurandiyl)}bis-tetrakis{(acetyloxy)methyl}ester.

12. The method of claim 11, wherein said sodium sensitive dye is sodium green tetraacetate, Na-sensitive Dye Kit or Fluorescent Membrane Potential (FMP).

13. The method of claim 1, wherein fluorimetric activity is measured by an ion flux assay.

14. The method of claim 13, which uses atomic absorption spectroscopy to detect ion flux.

15. The method of claim 1, wherein the human ENaC subunits are expressed under the control of a regulatable promoter.

16. The method of claim 1, which uses a fluorescence plate reader.

17. The method of claim 1, which uses a voltage imaging plate reader.

18. The method of claim 1, which is used to identify a compound that increases ENaC-dependent sodium or lung fluid absorption.

19. The method of claim 1, wherein the selected compound promotes sodium ion transport into taste bud cells.

20. The method of claim 1, which further includes testing the effect of derivative compounds of said ENaC enhancer compound in a human taste test.

21. The method of claim 1, which uses an automatic imaging instrument.

22. The method of claim 21, wherein said instrument is a fluorescence plate reader.

23. The method of claim 22, wherein said instrument is a voltage imaging plate reader.

* * * * *